(12) United States Patent
Lopes et al.

(10) Patent No.: US 10,261,042 B2
(45) Date of Patent: Apr. 16, 2019

(54) STATIONARY PROBE ROTATING DISK ELECTRODE

(71) Applicant: UChicago Argonne, LLC, Chicago, IL (US)

(72) Inventors: Pietro Papa Lopes, Lemont, IL (US); Nenad Markovic, Hinsdale, IL (US); Dusan Strmcnik, Woodridge, IL (US); Vojislav Stamenkovic, Naperville, IL (US)

(73) Assignee: UChicago Argonne, LLC, Chicago, IL (US)

( * ) Notice: Subject to any disclaimer, the term of this patent is extended or adjusted under 35 U.S.C. 154(b) by 102 days.

(21) Appl. No.: 15/280,878

(22) Filed: Sep. 29, 2016

(65) Prior Publication Data

US 2018/0088070 A1    Mar. 29, 2018

(51) Int. Cl.
*G01N 27/28* (2006.01)
*G01N 27/30* (2006.01)

(52) U.S. Cl.
CPC ........... *G01N 27/283* (2013.01); *G01N 27/30* (2013.01)

(58) Field of Classification Search
CPC .. G01N 27/30–27/304; G01N 27/307–27/308; G01N 27/31–27/32; G01N 27/33; G01N 27/34; G01N 27/36; G01N 27/40; G01N 27/401; G01N 27/403; G01N 27/4035; G01N 27/404; G01N 27/4045

USPC ........ 204/404, 409, 412, 415–420, 431–433, 204/435

See application file for complete search history.

(56) References Cited

U.S. PATENT DOCUMENTS

| | | | |
|---|---|---|---|
| 2003/0029726 A1* | 2/2003 | Kovarsky | C25D 21/12 205/81 |
| 2005/0035002 A1* | 2/2005 | Wang | G01N 27/403 205/775 |
| 2005/0082174 A1 | 4/2005 | Kendig et al. | |

OTHER PUBLICATIONS

Klemm et al., Coupling of a High Throughput Microelectrochemical Cell with Online Multielemental Trace Analysis by ICP-MS, 2011, 3 pages.

* cited by examiner

*Primary Examiner* — Bach T Dinh
(74) *Attorney, Agent, or Firm* — Foley & Lardner LLP

(57) ABSTRACT

A stationary probe having a probe holder and a probe with a probe tip. The stationary probe may be part of a stationary probe rotating disk electrode wherein the stationary probe has a passage therethrough for rotatably receiving a rotating disk electrode comprising a rotating shaft, rotatable about a longitudinal axis, and having an electrode portion extending therefrom configured to receive an electrode. The stationary probe rotating disk electrode may be part of an analytical system wherein the probe tip includes a capillary entrance spaced apart from the electrode and connected to an analyte flow path.

20 Claims, 21 Drawing Sheets

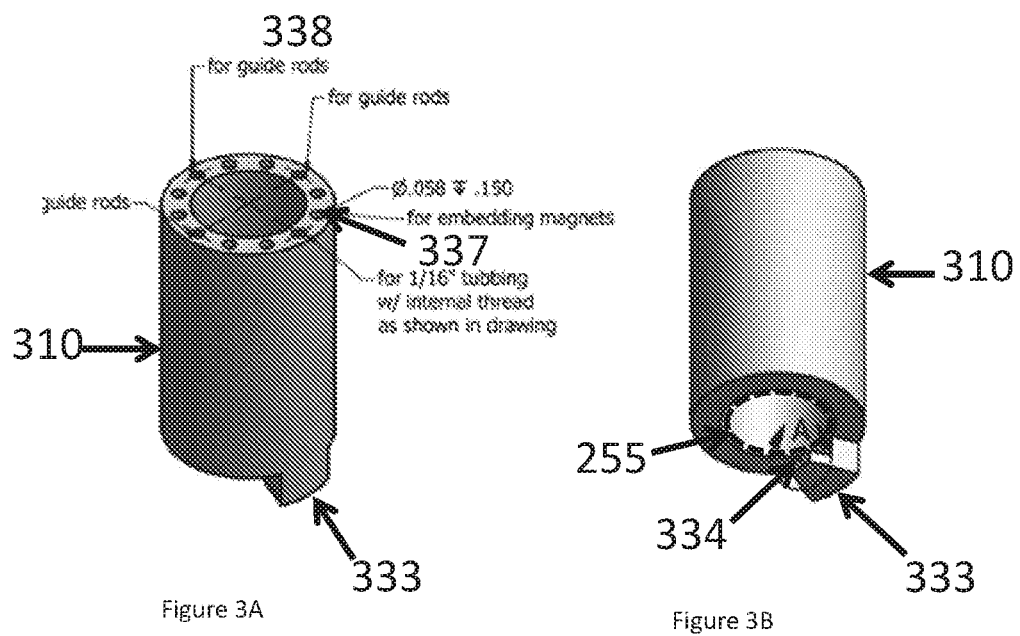
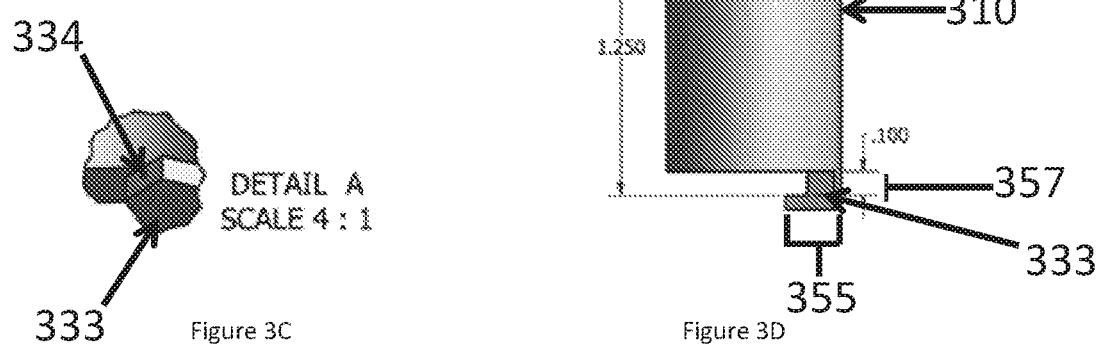

STATIONARY PROBE ROTATING DISK ELECTRODE

The United States Government claims certain rights in this invention pursuant to Contract No. W-31-109-ENG-38 between the United States Government and the University of Chicago and/or pursuant to DE-AC02-06CH11357 between the United States Government and UChicago Argonne, LLC representing Argonne National Laboratory.

TECHNICAL FIELD

The present disclosure relates generally to methods for electrochemistry and surface composition analysis.

BACKGROUND

Analysis of electrodes specifically and of materials in general is of grat importance. The development and improvement of materials, such as catalytic electrodes, relies upon the ability to analyze and understand the material and its function. Structure-activity relationships have been the basis for predictive ability in tailor-making nanomaterials with desirable reactive properties for some time. However, such an approach as disadvantages. A more robust approach to analysis would open new avenues of development.

Existing techniques for analysis provide some information regarding atomic and molecular level interactions of materials. For example, prior work has coupled a scanning flow cell (SFC) to an Inductively Coupled Plasma-Mass Spectrometer (ICP-MS), enabling in situ measurements of the dissolution of polycrystalline metal electrodes. By utilizing this method it was possible to establish relationships between potential-dependent oxide formation in various environments Despite the breadth of these experiments, knowledge of potential-induced surface stability at atomic-/molecular-levels still remains incomplete. Two key fundamental and technical barriers for this are that: (i) current in-situ ICP-MS methodologies are not sensitive enough to probe the stability of various defects such as ad-islands and step edges that are inherently present on single crystal surfaces and (ii) there is no experimental strategy capable of simultaneously monitoring stability-reactivity relationships at well-defined surfaces and at well-established diffusion/kinetic conditions. The development of such a methodology would offer the ability to embrace a science-based strategy capable of exploring, at atomic-/molecular-levels, the role of covalent and non-covalent interactions in metal dissolution/activity rates.

SUMMARY

Embodiments described herein relate generally to a stationary probe rotating disk electrode (SPRDE). The SPRDE comprises a stationary probe, with a passage therethrough, having a probe holder and a probe engageable with the probe holder, the probe having a probe body with a probe opening and a probe tip. A rotating disk electrode comprising a rotating shaft, rotatable about a longitudinal axis, and an electrode having a distal end with an electrode disposed therein, the rotating disk electrode rotatably positioned within the passage of the stationary probe with the electrode disposed within the probe. The probe tip extends from the probe body apart from the electrode and having a capillary entrance spaced apart from the electrode a first distance, the capillary entrance connected to an analyte flow path.

Some embodiments, relate to an analytical system comprising an analytical instrument having an analyte flow intake and a stationary probe rotating disk electrode (SPRDE). The SPRDE comprises a stationary probe having a probe holder and a probe with a probe body and a probe tip; a rotating disk electrode comprising a rotating shaft, rotatable about a longitudinal axis, and having an electrode portion extending therefrom configured to receive an electrode. The probe tip extending from the probe body apart from the rotating shaft at an electrode end and having a capillary entrance spaced apart from the electrode end a first distance, the capillary entrance connected to an analyte flow path. The probe holder configured to engage with the probe, the probe holder and probe having passage there through configured to receive the rotating shaft, the probe hold secured relative to the rotating disk electrode to define a distance between the electrode and the probe tip with the rotating shaft rotatable within the probe holder. The analyte flow path is in fluid communication with the analyte flow intake.

Some embodiments relate to a stationary probe comprising a probe holder and a probe. The probe holder and probe engagable by a plurality of alignment rods and a corresponding a plurality of openings and a plurality of magnets. The probe holder and probe having a passage therethrough configured to receive a rotating disk electrode assembly. The probe having a probe tip extending over the passage and having a capillary entrance connected to an analyte flow path.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 3A shows a view of the probe from the proximate end; FIG. 3B shows a view of the probe from the distal end; FIG. 3C is a close-up view of the capillary entrance of a probe of FIG. 3A at A-A; FIG. 3D is a side view of a probe.

FIG. 8(A) shows the effect of $Cl^-$ addition ($10^{-8}$ M $10^{-6}$ M, $10^{-5}$ M) on Pt(111) voltammetry profile 0.1 M $HClO_4$ up to 1.1 V, highlighting changes in both $OH_{ad}$ and $O_{ad}$ processes and its effect on Pt dissolution. Inset (8a') shows small but persistent decrease in overall Pt dissolution in the presence of trace levels of $Cl^-$ (below $10^{-5}$ M) due formation of $O_{ad}$ at higher potentials. FIG. 8(B) shows voltammetry and Pt dissolution profile in 0.1 M KOH solutions (KOH, KOH+$Li^+$, $HClO_4$) shows that addition of 5 mM $Li^+$ stabilizes $OH_{ad}$ through non-covalent interactions, reflecting in smaller dissolution of Pt due oxide formation at higher potentials when compared to bare $K^+$ solutions. Note that significant bulk speciation effects (complexation of Pt ions in solution) are present in alkaline media when compared to acidic electrolytes.

FIG. 12A shows polycrystalline silver electrode is used to provide constant dissolution at potentials above 0.6 V vs. RHE and analysis of the real time in situ dissolution measured by ICPMS as depicted in FIG. 12A can be used to obtain the N values plotted in FIG. 12B showing the dependence of N with electrode rotation values for a given flow rate ($f_{pump}$) and total cell solution volume ($V_{cell}$).

FIG. 13A is for Pt(111), FIG. 13B is for Pt(100), FIG. 13C is for Pt(Poly), and FIG. 13D is for Pt(nano) (TKK 3 nm), measured at the same experiment using the SPRDE connected to ICPMS. Note that increasing upper potential limit induces higher Pt dissolution as formation of Pt—$O_{ad}$ is increasing as well, at the same time that the nature of the Pt surface site and its coordination number are ultimately controlling oxide formation and the consequent Pt dissolution.

FIG. 14A is a graph of dissolution of Pt observed on Pt(111), which is dependent on surface preparation rather than atmosphere present in the cell (no changes between Ar or $O_2$ purged solutions). FIG. 14B is a graph of dissolution of Pt observed on Pt(nano), which is dependent on surface preparation rather than atmosphere present in the cell (no changes between Ar or $O_2$ purged solutions but at much higher concentrations than for FIG. 14A.

Figure 1:
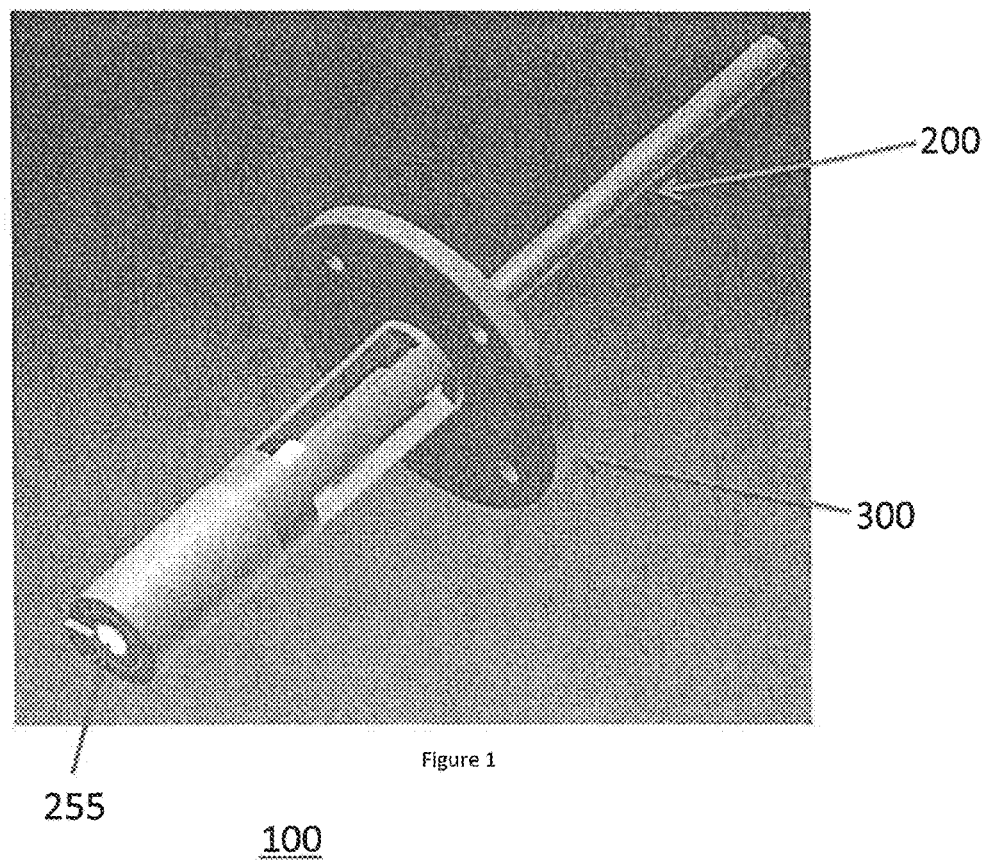
FIG. 1 shows one embodiment of a Stationary Probe Rotating Disk Electrode (SPRDE).

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Described herein are articles of manufacture and methods relating to a stationary probe (SP) with a rotating disk electrode-such as Pt(hkl)-(RDE) setup. The SP and RDE are, in one embodiment, coupled to an inductively coupled plasma mass spectroscope (ICP-MS) in order to study the role of surface geometry on the stability of surface atoms and enable "atom-by-atom" detection of the adsorbate-induced dissolution of Pt atoms in acidic and alkaline environments. As further discussed herein, it has been found that the degree of stability of Pt(hkl) surfaces [Pt(110)<<Pt(100)<Pt(111)] is proportional to the coordination of surface atoms. The results provide a clear link between the potential-dependent adsorption of covalently bonded oxygenated species and chloride anions in acidic solutions, as well as non-covalent interactions between adsorbed oxide and hydrated lithium cations in alkaline solutions. The overall dissolution rates are driven by a synergy between electrochemical (potential-induced oxide formation) and chemical (thermodynamic driving force for Pt complexation) corrosion. The dissolution dynamics are strongly affected by the nature of the electrochemical reaction; e.g., continuous dissolution occurs during the oxygen evolution reaction (OER), limited dissolution occurs during the CO oxidation reaction, and no dissolution takes place during the oxygen reduction reaction (ORR). The structure-stability relationships found for platinum single crystals can be used as a foundation for understanding the stability of polycrystalline Pt electrodes and Pt nanoparticles.

One embodiment of a stationary probe rotating disk electrode (SPRDE) setup is shown in FIG. 1. The SPRDE 100 consists of a consists of an rotating electrode assembly 200 and a stationary probe 300. In some embodiments the rotating electrode assembly 200 has a generally cylindrical cross-shape configured to correspond to a generally cylindrical passage 320 through the stationary probe 300.

Figure 2A:
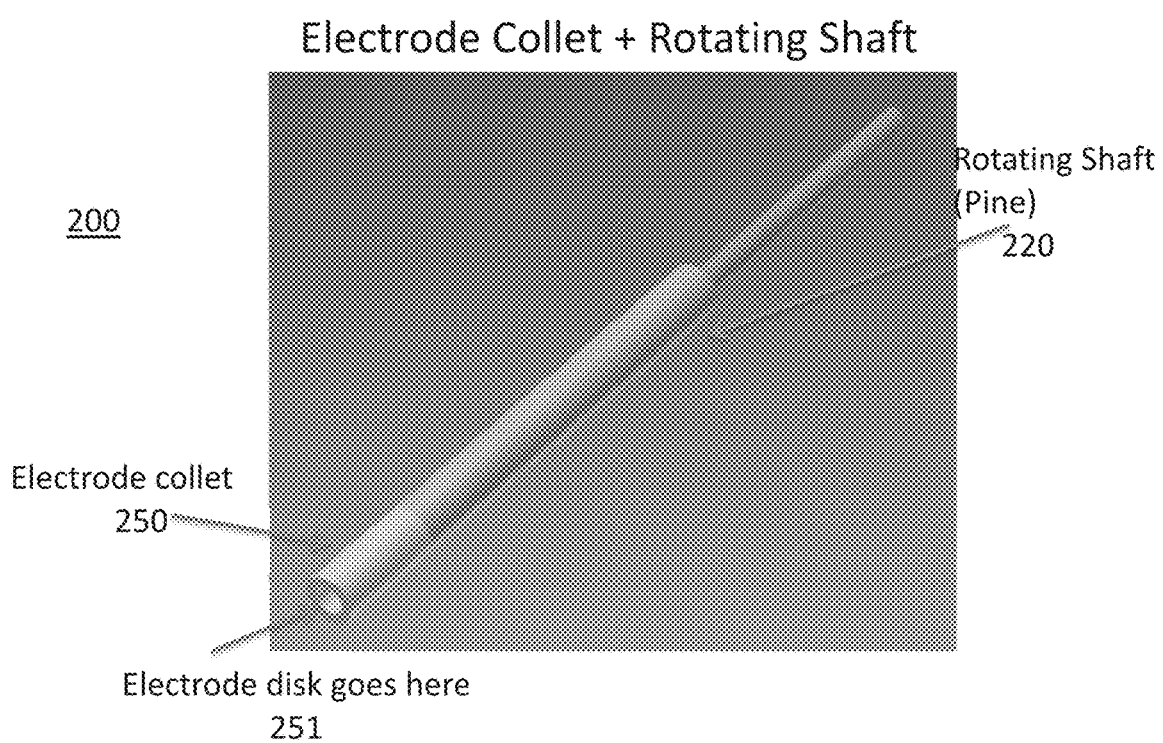
FIG. 2A shows a perspective view of a probe.

FIG. 2A illustrates one embodiment of a spinning electrode assembly. The rotating electrode assembly has a rotating electrode assembly body with a rotating shaft 220, and an electrode section 250. The rotating shaft 220 may be as known in the prior art for rotating disk electrode systems. The rotating electrode assembly 200 may be hollow, such as for accepting an electrode 255 and wiring or the like extending therefrom. The rotating shaft 220 is rotatable about a central longitudinal axis. As described herein the end of the SPRDE having the probe and electrode is considered distal and the opposite end, such as having the probe holder nut 325 is considered proximate.

Figure 2B:
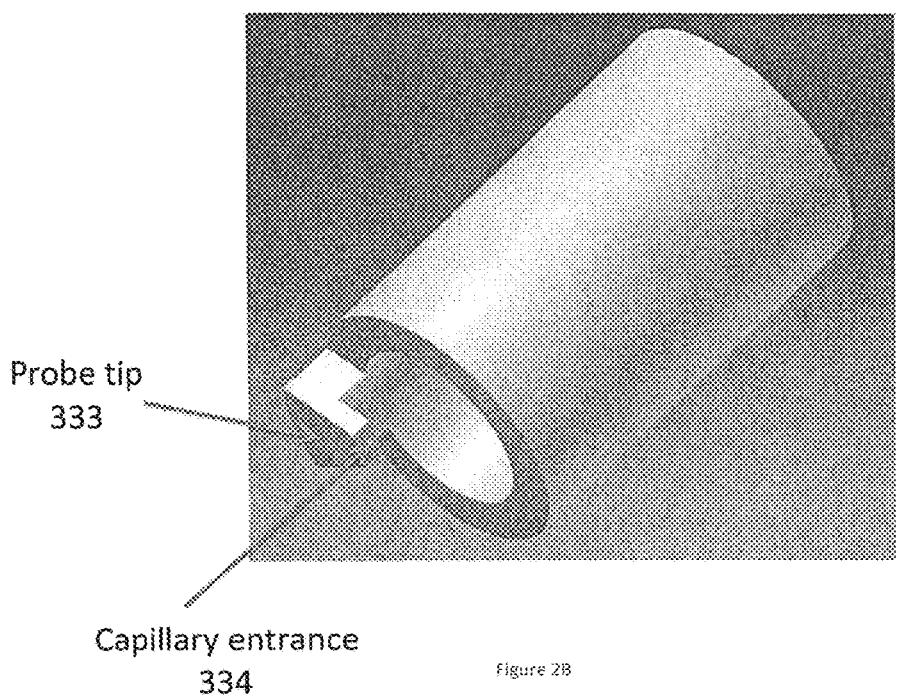
FIG. 2B shows a perspective view of the electrode section of the probe.

Disposed on or within the rotating electrode assembly body is an electrode 255. With reference to FIG. 2B, some embodiments include an electrode section 250 of the rotating electrode assembly 200 is shown. The electrode section 250 may be, for example, an electrode collet. The electrode 255 may be configured to engage the rotating shaft as is known in prior art rotating disk electrode systems. For example, in one embodiment, the electrode 255 maybe positioned by press fitting or the like in an electrode opening 251 of the rotating shaft 220 or within the electrode section 250. In some embodiments, the electrode 255 is part of a rotating disk tip that is engageable (and removable) with the rotating shaft 220. The electrode may be configured to engage with the rotating shaft 220 and, as such, may rotate with rotating shaft 220, and, in some embodiments rotates with the electrode portion 250. The electrode 255 has a size and shape configured to be so disposed in the probe. In some embodiments, the electrode 255 is selected not for its electrical conductivity (or lack thereof) but to present a surface material of interest. For example, the surface of the electrode 255 may present materials for dissolution or decomposition, which may be studied using the SPRDE. Further, the electrode may be comprised of a material to be studied or for providing an environment to be studied, for example the electrode 255 may comprise a material to be dissolved.

Figure 5A:
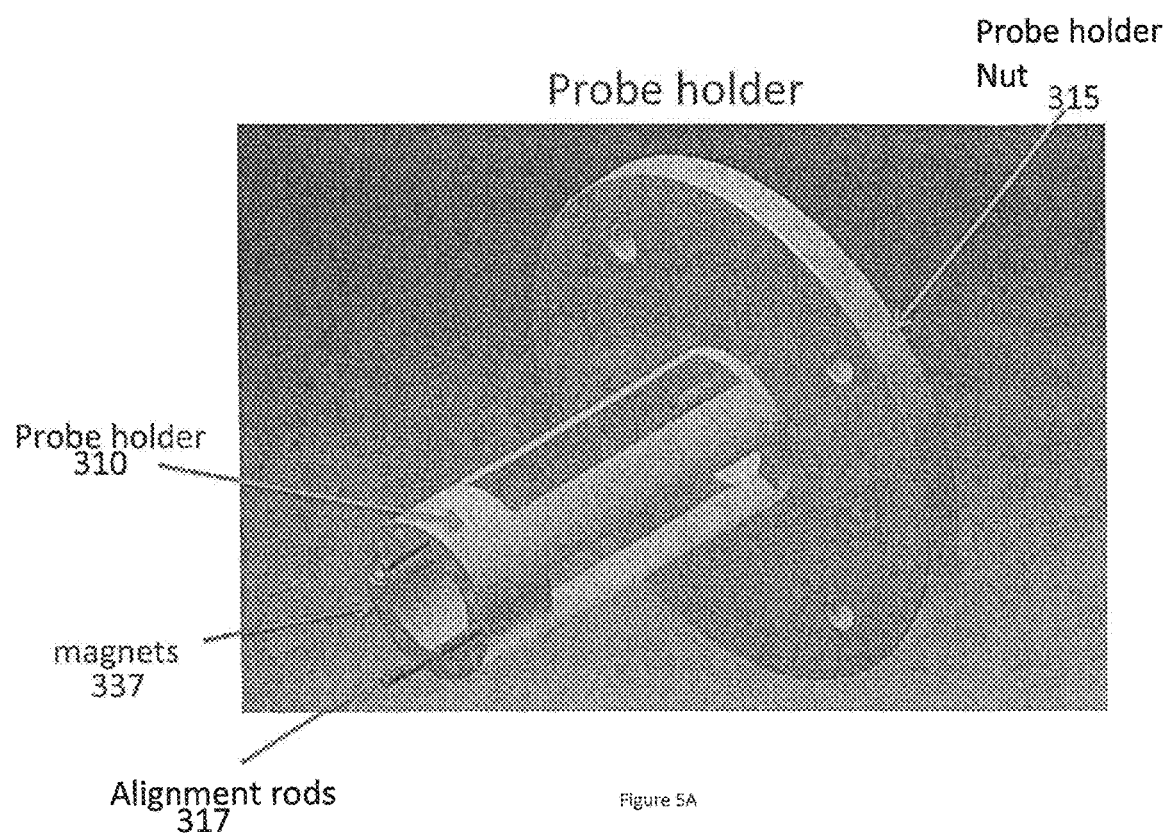
FIG. 5A is a perspective view of a probe holder.
Figure 5B:
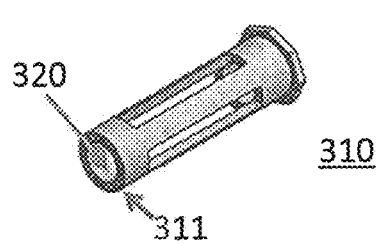
FIG. 5B is a perspective view of a body of a probe holder.
Figure 5C:
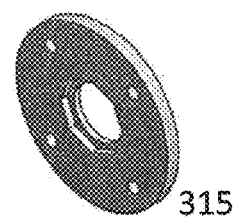
FIG. 5C is a perspective view of a probe holder nut.

The stationary probe 300 comprises a probe holder 310 and a probe 330. FIG. 5A illustrates one embodiment of a probe holder 310. The stationary probe 300 includes the probe holder 310 (best shown in FIG. 5B) with a probe holder nut 315 (Best shown in FIG. 5C) at one end and a rotating electrode assembly passage 320 passing through the probe holder body 310 and the probe holder nut 315. The probe holder body 310 is stationary and the rotating electrode assembly 200 is disposed to rotating inside the probe holder 310. The probe holder 310 may be secured relative to the rotating disk electrode assembly 200, such as to a base associated with the rotating disk electrode assembly 200 allowing rotation but fixing the position of the rotating disk electrode assembly relative 200 relative to the probe 330 and probe tip 333.

At a probe end 311 of the probe holder 310, a plurality of magnets 337 are provided. The magnets 337 may be embedded in the probe holder, such as flush with a surface at the probe end 311 or counter-sunk a distance from the surface. One or more alignment mechanisms, such as alignment rods 317 are provided at the probe end 311. In the embodiment illustrated in FIG. 5A, the alignment rods 317 extend beyond the probe end 311.

Figure 6:
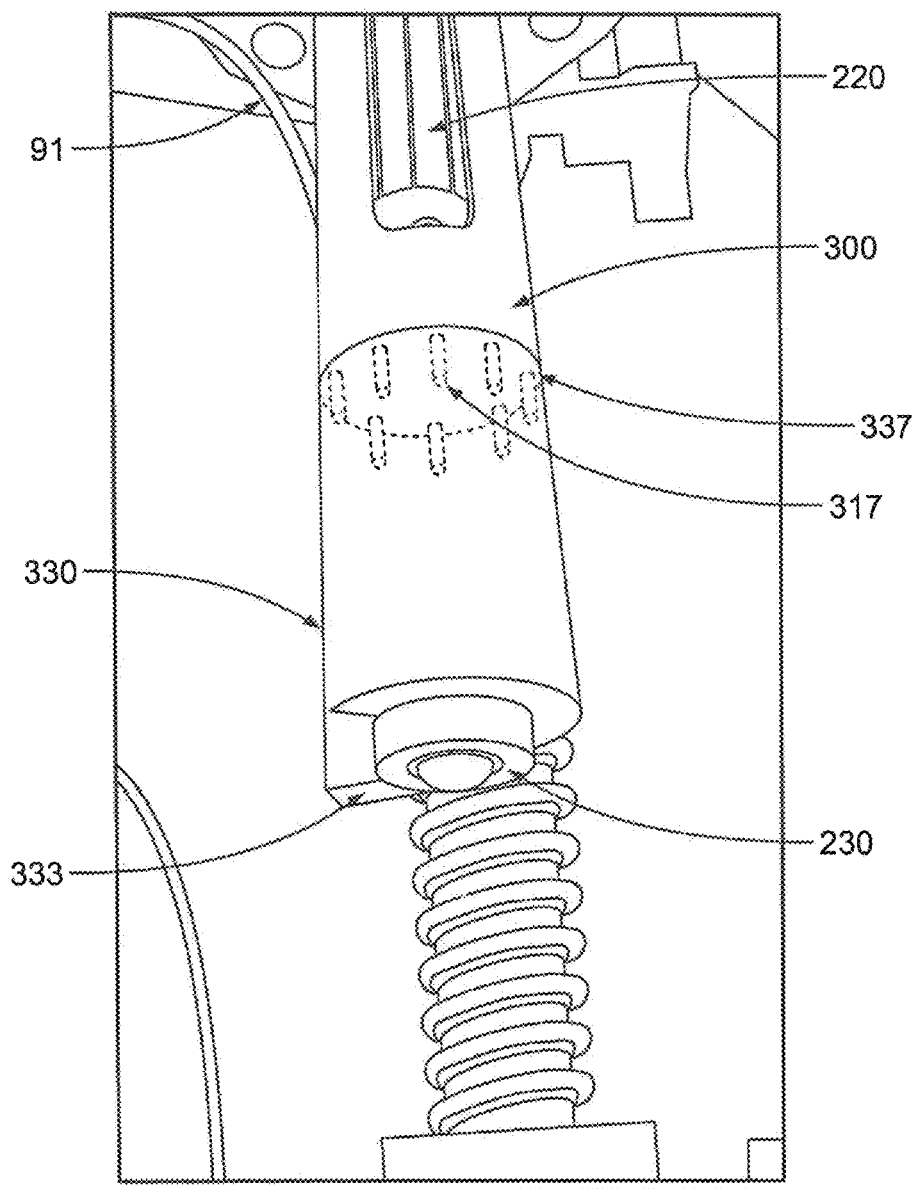
FIG. 6 shows a portion of a SPRDE.

FIG. 2A illustrates one embodiment of a probe 330. The probe 330 is secured to the probe holder 310 and does not rotate as best shown in FIGS. 1 and 6. In one embodiment, the probe 330 includes at a proximate end 332, for mating with the probe holder 310, a plurality of magnets 337. The magnets 337 may be embedded in the probe 330, such as flush with a surface at the proximate end 332 or counter-sunk a distance from the surface. FIGS. 3A-3D illustrate further details regarding one embodiment of the probe 330. In the illustrated embodiment of FIG. 3A, the proximate end 332 includes a surface having the plurality of magnets spaced thereabout as well as a plurality of openings 338 for receiving the alignment rods 317 of the probe holder 310 as further described below.

The probe 330 further comprises at a distal end 331 a probe tip 333 and a capillary entrance 334. The passage 320 within the stationary probe 300 may terminate with an probe opening 336 at the distal end 331. The electrode 255 may be positioned within the opening 336 in the probe 330 In some embodiments, the electrode section 250, acting as a collet, is positioned within the probe 330 and supports the electrode and rotatable relative to the probe 330.

The probe 330 includes a probe tip 333 extending out from a probe body 335 (at the periphery or outer circumference) and extending inward (toward the center, from the periphery) above the electrode 255. The probe tip 333 extends inward a first distance 355 from the circumference of the probe body 335 and extends above the electrode a second distance 357. In some embodiments, more than one probe tip 333 is included FIGS. 3B and 3D best illustrate one embodiment of positioning of the probe tip 333 and the capillary entrance 334. The probe tip position is defined with respect to the axis of the system to the edge of the electrode 255. For example, in some embodiments the size is defined for standard electrode sizes for example 3-8 mm, such as 5 mm or 6 mm outer diameter crystals.

In one embodiment, to avoid any height adjustments between the probe 330 and electrode 255, as it would change collection efficiency (N), components are precisely machined, and such that the electrode is easily inserted into the electrode portion 230 or the rotating shaft 220 (Pine Instruments MSR). This setup leads to N values with no more than 5% variation between each experiment. Further, in some embodiments the electrode portion 230 and probe body 335 are machined to within some tolerance, typically to render the electrode portion 230 slightly longer than the probe body 335 so the probe tip 333 would sit flush or nearly flush to the electrode portion 230.

Figures 4A, 4B:
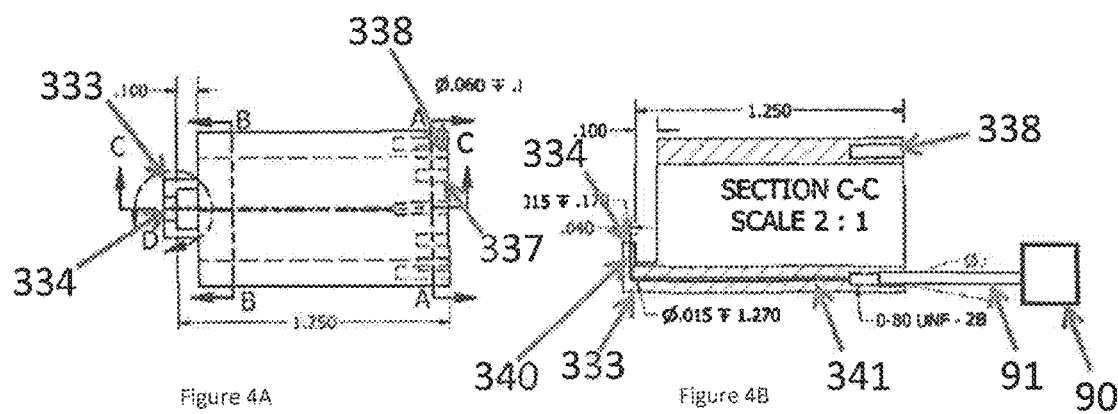
FIG. 4A is a side view of a probe.
FIG. 4B is a cross-sectional view along axis C-C of FIG. 4A.
Figures 4C, 4D:
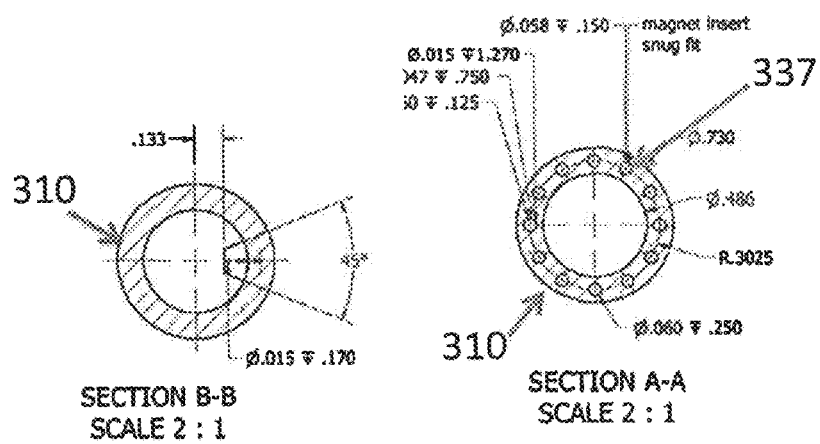
FIG. 4C is a cross-sectional view along axis B-B of FIG. 4A.
FIG. 4D is a cross-sectional view along axis A-A of FIG. 4A.

FIGS. 4A-D illustrate further details of the probe 330. FIG. 4A is a side view illustrating the location of the cross sections of FIG. 4B-4C. In one embodiment, shown in FIG. 4B, the capillary entrance 334 extends into a analyte flow path 341. The analyte flow path 341 may be engagable with a tubing 91 or the like to connect with the analytical instrument 90. In the embodiment of FIG. 4B, the capillary tube 340 is a PCTFE capillary tube (400 μm ID) positioned at the edge of the electrode 255 with electrolyte flow direction perpendicular to the electrode's 255 surface normal direction. Each probe tip 333 may have an associated analyte flow path and/or capillary tube 340.

The position of the probe tip 333 is defined at the edge of the electrode 255, as described above, to maximize collection of species from the electrode surface. The electrode 255 can rotate clockwise or counterclockwise and would not matter for the collection of species through the probe 330. However, the capillary entrance should be aligned to the center of the probe body 335.

The capillary 340 is machined or produced inside the probe body 335 and probe tip 333 designed to provide minimum flow path to the instrument. The selection of material is defined as to withstand chemicals and temperature as well as the capability of being machined of the possibility of 3d printing can also be contemplated. For example, PCTFE provides the excellent chemical compatibility of Teflon based materials with rigidity and machinability enough to be produced and utilized without any issues as to changes in its size and dimension with use. Further, the capillary entrance 334, analyte flow path 341, and tube 91 may be engineered to for fluid flow.

The tubing can be connected to any instrument in the most convenient way to the instrument. Whether regular fitting or any other coupling is fine, as long as it does not restrict the flow or alter the flow conditions dramatically.

In one embodiment, the alignment rods 317 aid in correctly orienting the probe 330 and the holder 310 by engaging with corresponding openings on the probe 330. The alignment rods 317 may extend from the probe 330 or the holder 310 and with the corresponding openings being on the other. Further, in one embodiment, the probe 330 is retained to the probe holder 310 by interaction of the respective plurality of magnets 337.

As best shown in FIGS. 1 and 6, in one embodiment the rotating disk electrode 200 and the stationary prober 300 are engaged with each other to form an assembled SPRDE system 100.

In one embodiment the probe holder 310 may include one or more openings between the distal end (or probe end) 311 and the proximate end 312. These one or more openings align with all or a portion of the rotating shaft 220.

As described above, the SPRDE 100 is coupled with an instrument 90. The instrument may be any that readily accepts liquid as an inlet. For example, the aforementioned ICPMS, as well as gas chromatography and liquid chromatography devices and ultraviolet-visible spectroscopes and infrared spectroscopes. Crystal preparation procedures and electrochemical measurements are executed the same way as described in previous publications (see, for example, Li, D.; Wang, C.; Strmcnik, D. S.; Tripkovic, D. V.; Sun, X.; Kang, Y.; Chi, M.; Snyder, J. D.; van der Vliet, D.; Tsai, Y.; Stamenkovic, V. R.; Sun, S.; Markovic, N. M. Energy Environ. Sci. 2014, 7 (12), 4061-4069.)

Experimental Results

Experiments were performed using a SPDRE in combination with a ICP-MS device, specifically a Perkin Elmer ICP-MS instrument (NexION 300D).

ICP-MS Measurements

The electrolyte is pumped out of the electrochemical cell with an ESI MP2 micro peristaltic pump at 7.5 μL s$^{-1}$ by the probe capillary connected to a PEEK tube (200 μm ID), all the way to the ICP-MS inlet system. The ICP-MS inlet is comprised of a Meinhard nebulizer (1.1 Lpm of Argon as nebulizing gas) and a cyclonic spray chamber. The flow rate was optimized to minimize the transport time between the electrode surface and the ICPMS detection (delay time ~5.5 s and total internal volume ~42 μL) while preventing bubble formation inside the capillary as observed at higher flow rates. Fresh electrolyte is replenished to the cell at the same flow rate to keep the total cell volume (~60.0 mL) constant. Plasma parameters were set to 1600 W RF power, 15.6 Lpm plasma flow rate and 1.0 Lpm auxiliary gas. The Pt signal was measured at m/z=195 a.m.u with 200 ms dwell time and ArCl$^+$ (75 a.m.u) or ArK$^+$ (80 a.m.u) dimers, generated inside the plasma from HClO$_4$ and KOH solutions, respectively, were used as internal standard with 50 ms dwell time (total of 0.25 s per replicate). The intensities were calibrated by immersing the SP in external solutions containing Pt in the electrolyte of interest prior to each experiment. An external trigger signal from the potentiostat (Autolab PGSTAT 302N) was set to initiate ICPMS data collection, ensuring synchronicity between Pt intensity and electrode potential changes over time.

Electrochemical Measurements

As a brief summary of electrode preparation and electrochemical measurements, all Pt(hkl) and Pt(poly) crystals were annealed up to 1100° C. in an 3% H$_2$/Ar atmosphere for 10 minutes. After slow cooling, a drop of ultra-pure deionized water (Milli-Q) was placed on the crystal surface before assembly into the RDE setup and transfer into the electrochemical cell. Detailed ex situ STM analysis of Pt(hkl) surface can be found in previous publications. 3 nm Pt nanoparticles (TKK) were dispersed in ultra-pure deionized water (~0.5 mg mL$^{-1}$) and sonicated for 30 minutes before a 30 μL drop was added to a polished (<0.5 μm) glassy carbon electrode already inserted in the RDE setup. After drying the ink, the electrode was rinsed with water to remove any loose particles. The catalyst loading was between 10-20 μg cm$^{-2}$. All solutions were prepared with ultra-pure deionized water to make 0.1 M HClO$_4$ (EMD, omnitrace ultra) and 0.1 M KOH (Fluka, 99.995%). Solutions containing chloride or lithium were prepared from appropriate dilution of concentrated HCl (EMD, omnitrace) or 0.1 M LiOH (Fluka, 99.995%), respectively. All gases (Ar, $O_2$ and CO) were 5N5 quality acquired from Airgas. Carbon rods (99.995%) were used as a counter electrode to avoid any metal contamination, and Ag/AgCl as reference electrode, noting that all electrode potentials are given versus the reversible hydrogen electrode (RHE), calibrated using $H_2$ oxidation in a separate experiment. All experiments were corrected for iR drop within the cell. After assembly of the RDE shaft into the rotator, the SP is inserted into the holder and the SPRDE setup is immersed in the electrolyte at controlled potential (ca. 0.05 V vs. RHE) simultaneously measuring Pt intensity with ICPMS. After immersion, first voltammetric scan was recorded together with Pt signal at sweep rate of 50 mV s$^{-1}$. All experiments were performed at room temperature (T=25° C.) and 100 rpm electrode rotation rate, except when otherwise noted.

Structure-Stability Relationships for Pt(Hkl)

In situ SPRDE-ICPMS studies were undertaking on the potential-dependent formation and reduction of oxide films on Pt(hkl) single-crystals, polycrystalline Pt, and Pt nanoparticles, in acidic aqueous solutions, and the associated dissolution of Pt during positive- and negative-going potential sweeps.

There are four key advantages to the described SPRDE-ICPMS method as compared with other methods developed in the past. First, it provides almost an order of magnitude higher sensitivity for metal dissolution as compared with the SFC-ICPMS studies mentioned above (e.g., 0.4 pg cm$^{-2}$ s$^{-1}$ in this work vs. 3 pg cm$^{-2}$s$^{-1}$ in ref. 6).

Second, the RDE configuration permits control over mass transport properties at the electrode surface that allow establishment of correlations between the structure-sensitive adsorption of covalently bonded species on well-defined single crystal surfaces and the stability of surface atoms on those surfaces. Third, the well-defined surfaces allow for explorations of the synergetic role of covalent adsorbate-substrate interactions and non-covalent interactions (operating in the double layer) in guiding the corrosion of metal surface atoms. Finally, the SPRDE-ICPMS method enables the in situ measurement of activity-structure-stability relationships—functional links that have never been studied thus far at atomic/molecular level.

Figure 7A:
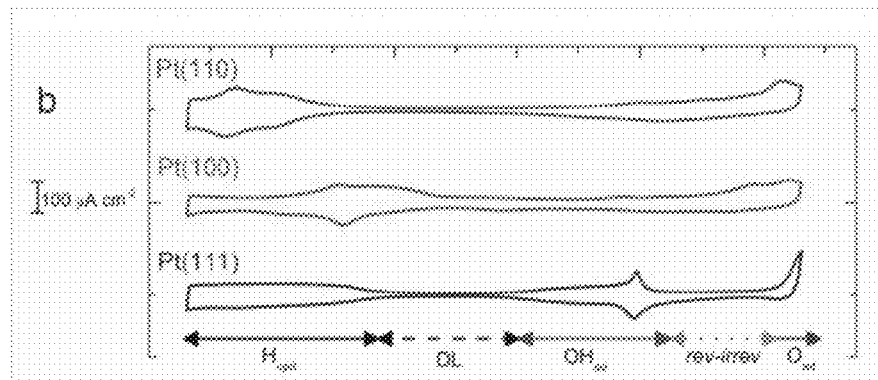
FIG. 7(A) is a graph showing voltammetric profile of Pt(110), Pt(100), and Pt(111) surfaces.

Displayed in FIG. 7A typical cyclic voltammograms (CVs) of Pt(110), Pt(100) and Pt(111) in 0.1 M HClO$_4$ in the potential range between 0.05 to 1.05 V. Varying the positive potential limit is sufficient to provide information about the influence of the nature of oxygenated species on the stability of Pt surface atoms. In agreement with the literature, on all three single crystal surfaces the hydrogen adsorption potential region (Pt+H$^+$+e$^-$↔Pt—H$_{ad}$) is followed by the adsorption of OH$_{ad}$ (Pt+H$_2$O↔Pt—OH$_{ad}$+H$^+$+e$^-$) and, finally, by irreversible oxide formation (PtOH$_{ad}$→PtO$_{ad}$+H$^+$+e$^-$). While the interaction of OH$_{ad}$ with platinum involves orbital overlap and covalent bond formation with zero formal net charge (Pt$^{\delta+}$—OH$_{ad}$$^{\delta-}$), the reversible-irreversible transition encompasses a change in the valence state of Pt and formation of an oxide in which Pt is a positively charged cation. FIG. 7A also shows that the onset potential for irreversible oxide formation strongly depends on the geometry of Pt surface atoms, increasing in the same order as the coordination number of surface atoms Pt(110)<Pt(100)<Pt(111). Since the reversible-irreversible oxide transition is only clearly defined for Pt(111), the primarily focus was on structure-activity/stability relationships for this surface.

FIGS. 13A-13D show cyclic voltammetry and the corresponding in situ dissolution profiles obtained with SPRDE-ICPMS on Pt(111), Pt(100), Pt(Poly) and Pt(nano) (TKK 3 nm) in 0.1 M HClO$_4$ solution. The main electrode processes are observed for all Pt surfaces in perchloric acid solutions, highlighting that only the formation of irreversible oxide triggers dissolution of Pt. This becomes evident for increasing electrode potential, leading to higher "true oxide" coverages that ultimately lead to higher overall Pt dissolution. Note that Pt(111) shows the same amount of Pt dissolution as observed from Pt(Poly) just after going 150 mV more positive in the anodic sweep. However, the nature of surface sites dictates the strength of Pt—O interactions, inducing the observed surface structure dependence of dissolution as a consequence of oxide formation. Therefore, the stability of Pt atoms increases for highly coordinated surface sites, e.g. stability increases in the order Pt(nano)<Pt(110)<<(PtPoly)<Pt(100)<Pt(111).

For Pt(111), the hydrogen adsorption region below 0.4 V and the adsorption of hydroxyl species between 0.65 to 0.85 V (traditionally referred to as the "butterfly feature) is separated by a wide double layer potential region. The butterfly region is followed by yet another "double-layer-like" potential region where the transition from reversible to irreversible oxide formation occurs above 1.0 V.

Figure 7B:
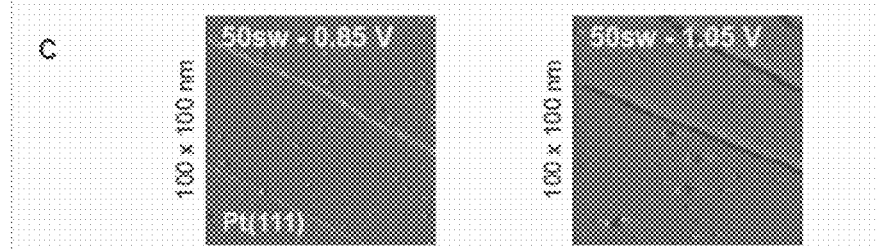
FIG. 7(B) shows selected STM images for Pt(111)

Selected STM images in FIG. 7B are shown to demonstrate that if the Pt(111) electrode is cycled between 0.05 V and 0.85 V, then no visible differences in surface morphology are observed between the pristine and cycled electrode; e.g., wide terraces decorated with a few ad-atoms are separated with monoatomic steps. Both CVs and STM images recorded after a few potential sweeps between 0.05 to 1.05 V show no visible differences with the corresponding CV/STM data recorded for the pristine surface. However, the first noticeable changes in surface morphology (formation of pits on wide terraces) are observed after 50 potential cycles up to 1.05 V (FIG. 7B).

Figure 7C:
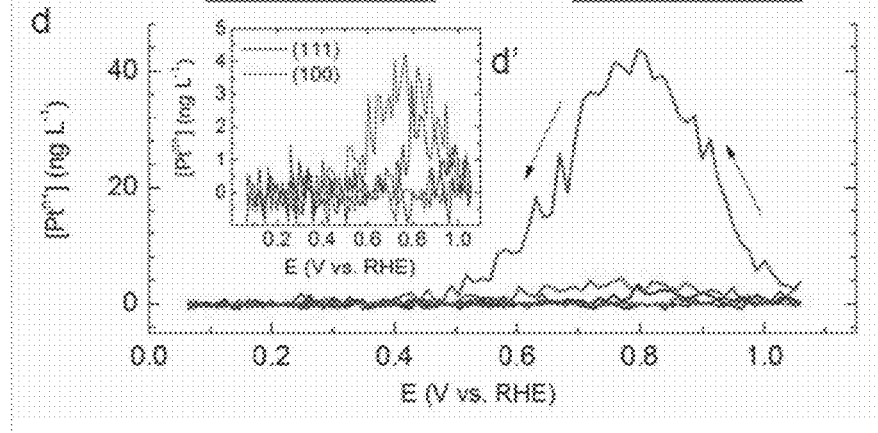
FIG. 7(C) shows the corresponding dissolution profiles for the above mentioned surfaces in 0.1 M $HClO_4$, highlighting the surface structure-dependence of the Pt dissolution process. (d') Inset emphasizes the large difference between dissolution observed on Pt(111) and Pt(100) from that on Pt(110).
Figure 14A:
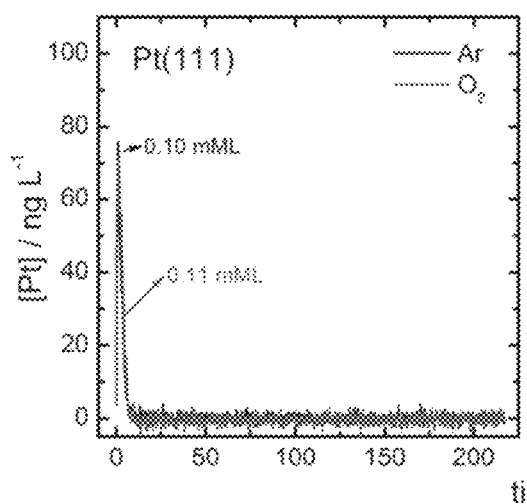
FIG. 14A-B shows in situ monitoring of Pt dissolution upon immersion of the electrode at controlled potentials.
Figure 14B:
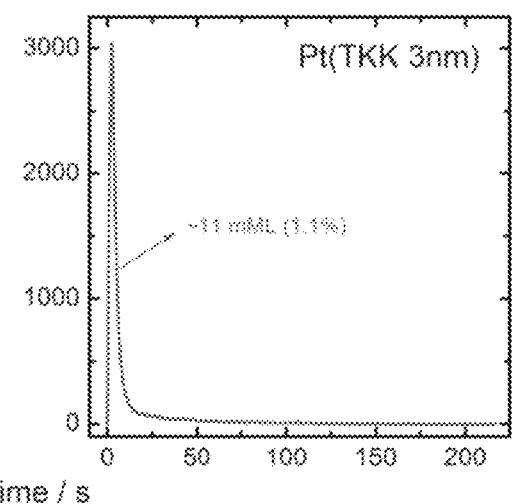

Having established "rough" limits to the stability of the Pt(hkl) surface structure under various potential treatments, the experiments focused then on processes associated with the fine-scale, structure-sensitive dissolution of Pt(hkl) in 0.1 M HClO$_4$. It should be noted that the ICP-MS data summarized FIG. 7C are collected during the very first potential sweep, corresponding to CVs depicted in FIG. 7A. This is important to emphasize considering that the reactivity of Pt(hkl) is strongly dependent on the experimental history (vide infra). Three observations are noteworthy. First, it was observed the instantaneous dissolution of a small, yet clearly discernable, amount of Pt surface atoms upon the immersion of Pt(hkl) in the electrolyte at 0.05 V (FIG. 14A-B), suggesting that some surface atoms are rather unstable even at 0.05 V. Second, after this initial dissolution the electrode is rather stable, even upon 50 potential sweeps between 0.05 and 0.85 V. Upon immersion of the electrode in solution, continuous monitoring of Pt ions shows a transient process in which some surface atoms are released upon contact with electrolyte. As shown in FIG. 14A-B, this process is not dependent on cell atmosphere, e.g. the transient dissolution is not induced by reduction of oxygen that might be present in the cell, but rather is dictated by the surface preparation procedure. Although the procedure of high temperature annealing and surface protection by a drop of ultra-pure water is rather standard and frequently used by many in the field, our results shows that some small oxidation of surface atoms that leads to dissolution upon immersion are always present. Dissolution upon immersion is even more severe for nanoparticle electrodes, which might be of concern for real-world highly tailored surfaces, as defects induced by dissolution upon immersion could be detrimental to the overall effect expected from tailor making the nanoparticle surface.

It is obvious then, that the structure-sensitive reversible adsorption of $OH_{ad}$ is not powerful enough to trigger the dissolution of Pt surface atoms. It is likely that the initial dissolution of pristine Pt observed upon immersion at 0.05 V is related to the formation of other types of surface oxides than $OH_{ad}$. Third, although the Pt(111) surface is stable during the first positive (anodic) sweep, structure-sensitive dissolution of Pt surface atoms is observed on the subsequent reverse (cathodic) sweep. This same profile is observed on all other Pt surfaces and the amount of dissolution increases in the opposite order of the coordination of surface atoms, with Pt(110)>>Pt(100)>Pt(111) as summarized in FIG. 7C and Table 1. As adsorption energies for both $OH_{ad}$ and $O_{ad}$ increases at low coordination sites but Pt dissolution is observed only after oxide formation/reduction, our results show unambiguously that the dissolution of Pt is controlled by the nature of Pt atoms (stable $Pt^{\delta+}$ vs. unstable $Pt^{n+}$), and that structure-sensitive dissolution is dependent on formation of oxide at lower potentials. In turn, it is reasonable to anticipate that the surprising dissolution of Pt observed upon immersion in electrolyte at 0.05 V is the consequence of the reduction of an irreversible-type oxide that is formed during preparation of the Pt electrode for electrochemical measurements.

Figure 15:
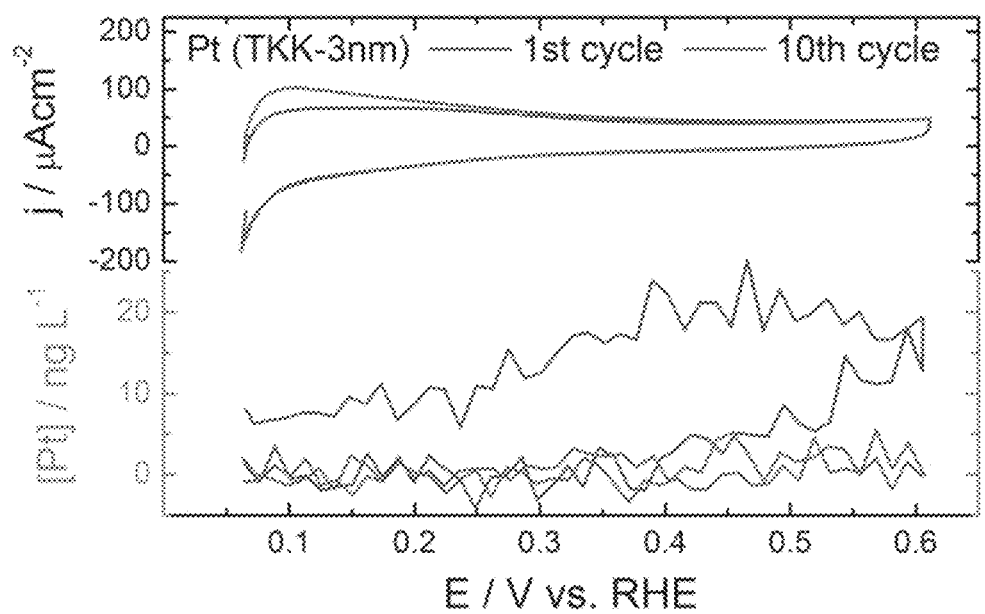
FIG. 15 illustrates first scans on Pt(nano) showing differences in both voltammetric and dissolution profiles at first and tenth continuous sweep. Note that Pt dissolution is already observed even in the anodic scan for the very first potential cycle at electrode potential much earlier than expected for Pt—$O_{ad}$ formation.
Figure 16:
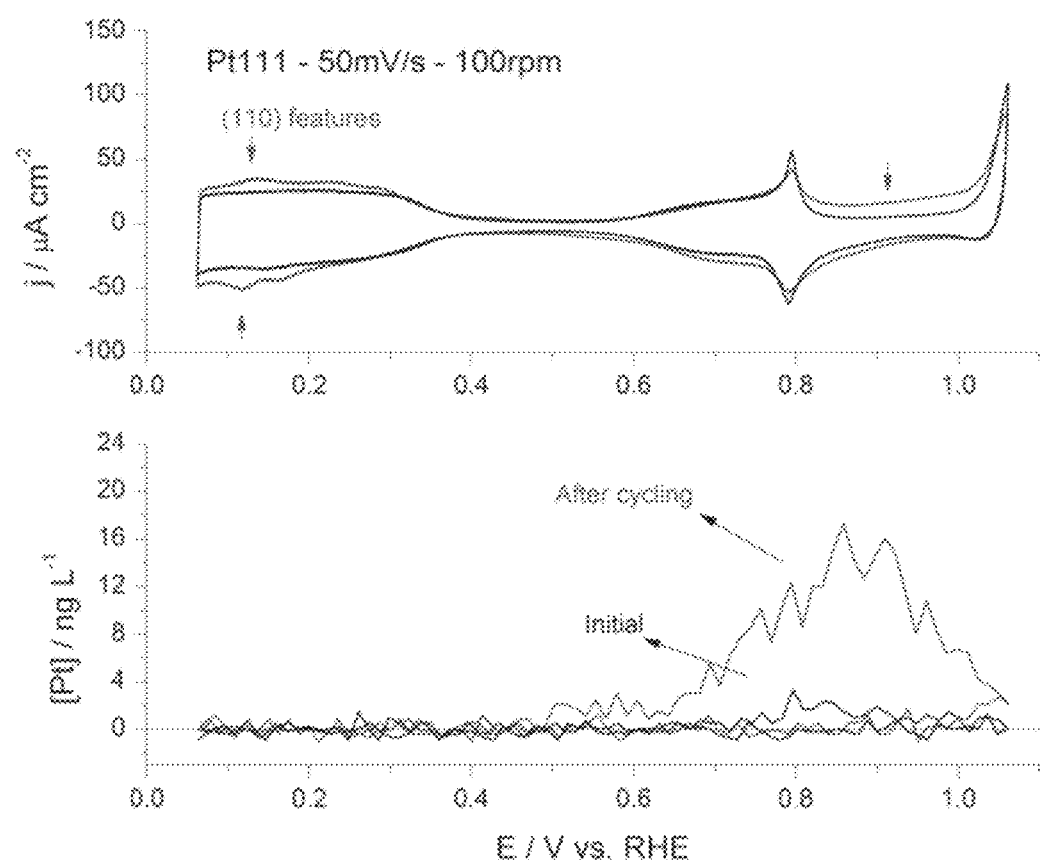
FIG. 16 illustrates the effect of surface roughening on Pt(111) monitored by cyclic voltammetry and SPRDE-ICPMS. Initial scan shows a typical clean, well-oriented Pt(111) surface, but barely touching Pt—$O_{ad}$ formation already shows Pt dissolution signs that can be monitored by SPRDE-ICPMS, but that detected by voltammetry only after several continuous cycles (more than 50 scans), showing extra features related to Pt(110)-like sites.

Further inspection of Table 1 reveals that polycrystalline Pt (Pt-poly) is much more stable than Pt nanoparticles (Pt-nano), which is not surprising considering that Pt-nano contains a very high level of low-coordination surface atoms. As a consequence, and in contrast to Pt(111), it was observed that the first scan of Pt-nano is not stable even at 0.6 V, although stabilization occurs after each consecutive cycle (FIG. 15). Certainly, developing real-world catalysts with highly tailored surfaces must take into account these initial dissolution processes in order to meet more stringent stability targets. Because the amount of dissolved Pt under our experimental conditions is very small (2±1 micromonolayers, µML) it is not surprising that neither STM nor CV are able to detect any significant morphological/voltammetric changes during the initial potential cycles. Based on these results alone, it is obvious that our SPRDE-ICPMS method can provide more information about the stability of surface atoms than STM. As expected, subsequent potential sweeps up to 1.05 V are always accompanied by the dissolution of a small number of platinum surface atoms, leading to a cumulative roughening of the Pt(111) surface and eventually resulting in pit formation after 50 dissolution/redeposition cycles (FIG. 7B). This roughening is also associated with changes in the $H_{upd}$ profiles in the CV (FIG. 16). As discussed, the high sensitivity of the SPRDE probe enables detection of Pt dissolution during the early stages of Pt oxide formation that are not reflected in any significant features in cyclic voltammetry. FIG. 16 shows the initial Pt(111) electrode voltammetry and its corresponding dissolution profile. Note that dissolution from one single scan can be detected by SPRDE, indicating that surface changes are already taking place, whereas voltammetry only detects these changes after several cycles (more than 50). As a consequence, the indication by CVs that surface morphology is not the same as the initial, well-oriented Pt(111) is reflected in the higher overall Pt dissolution, as shown in FIG. 16, and stability is closely related to surface site coordination number.

Overall, then, the results summarized in FIGS. 7A-C demonstrate that in situ SPRDE-ICPMS probe is capable of exploring structure-stability relationships with unprecedented sensitivity. It also provides clear-cut evidence that although specifically adsorbed $OH_{ad}$ has no effect on the stability of Pt surface atoms, surface coverage by even minute amounts of a true oxide is enough to trigger the dissolution of Pt during the reduction process. The question arises as to how co-adsorption of other, stronger, specifically adsorbed anions, such as may affect the potential stability range of Pt surface atoms.

Surface Stability Dependence on Covalent and Non-Covalent Interactions

The interaction of chloride with Pt(hkl) ($Pt+Cl^-_d \rightleftharpoons Pt^{\delta+}-Cl_a^{\delta-}+e^-$) has been studied extensively in the past. In the case of Pt(111), although no in-plane structure has been observed over the entire potential range between 0.05 to 1.0 V, the Pt—$Cl_{ad}$ bond length (2.4 Å) is consistent with the presence of a covalently bonded $Cl_{ad}$ adlayer with zero formal net charge. An interesting aspect of the specifically adsorbed $Cl_{ad}$ is that it can modify/block the adsorption of $OH_{ad}$ and inhibit irreversible oxide formation. This, in turn, provides an opportunity to explore how the coupling of chloride adsorption with irreversible oxide formation affects the dissolution of Pt surface atoms. Given that Pt corrosion is known to be enhanced by the strong complexation of Pt with $Cl^-$ present in the bulk of electrolyte, it would also allow us to simultaneously explore the role of surface speciation and bulk complexation, but on well-characterized single crystal surfaces.

Figure 8A:
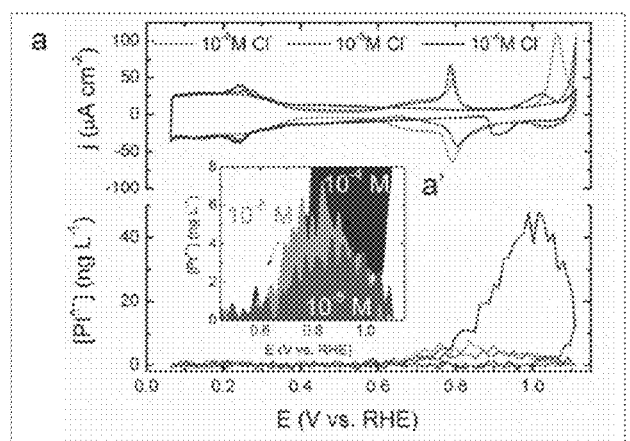
FIGS. 8(A)-8(B) show effects of covalent and non-covalent interactions in $OH_{ad}$ layer stability and its correlation with Pt dissolution.

The effect of the $Cl^-$ anion concentration on Pt dissolution during anodic and cathodic sweeps is summarized in FIG. 2a for $Cl^-$— free 0.1 M $HClO_4$ and in the presence of $10^{-5}$-$10^{-3}$ M $Cl^-$. It should be note that the CVs shown are again from the first positive sweep after immersion at 0.05 V. In agreement with previous work, the onset potential for irreversible oxide formation systematically shifts positive with increasing $Cl^-$ concentration, with the adsorption of $OH_{ad}$ eventually becoming completely blocked at higher concentrations of $Cl^-$. It should be noted that there is no dissolution of Pt observed during the first potential cycle between 0.05 to 0.8 V, presumably owing to the fact that Pt is still in the zero valence state in this potential range. As the positive potential window is opened beyond 1.05 V (ca. 1.1 V FIG. 8a and up to 1.15 V Table 2), the effect of $Cl^-$ anions on Pt dissolution becomes pronounced. For example, below $Cl^-$ $10^{-5}$ M dissolution of Pt takes place only during the negative-going sweep, a phenomenon that is also observed in the $Cl^-$-free electrolytes (FIGS. 7A-C). Furthermore, the total amount of dissolved platinum in $Cl^-$-free and $Cl^-$-containing solution (FIG. 8a and Table 2) is very similar, although total Pt loss is slightly less in trace levels of $Cl^-$ up to 1.1 V due less oxide formation, suggesting that under these experimental conditions the dissolution is still mainly governed by oxide-induced corrosion of Pt surface atoms and not due to Pt—$OH_{ad}$ or Pt—$Cl_{ad}$. For $Cl^-$ concentrations above $10^{-4}$ M, however, Pt dissolution is also observed on the positive sweep and starts at ~1.05 V (FIG. 8a). Note that the characteristic "butterfly" region also disappears at this Cl concentration, but that Pt dissolution follows only after the formation of $Pt^{n+}$—$O_{ad}$, which begins during the anodic sweep due to the well-established strong thermodynamic driving force for $Pt^{2+}$ complexation with dissolved chloride anions and the formation of soluble chloroplatinic acid. As shown in Table 2, this strong complexation effect is even more pronounced at higher concentrations of chloride anions (>$10^{-4}$ M). Taken altogether, the observed enhancement of Pt dissolution in the presence of $Cl^-$ is triggered by the combined action of irreversible oxide formation and Pt complexation with dissolved chloride anions.

Figure 8B:
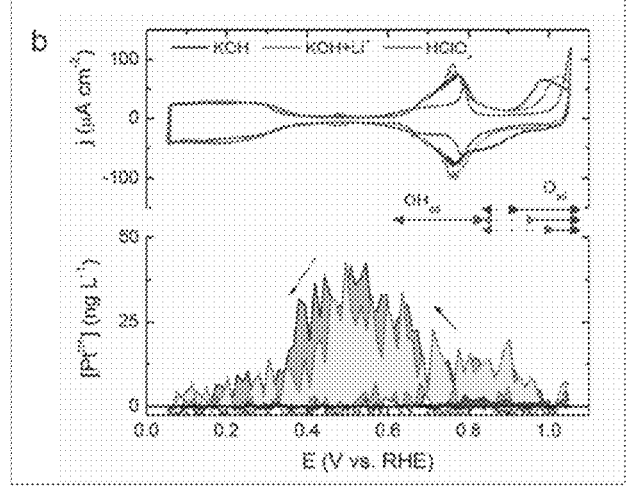

Having thus far focused on the role of covalent interactions in oxide formation resulting in Pt dissolution, the next consideration is whether the rather weak, non-covalent interactions that take place in the double layer may also play a role in determining the stability of platinum surface atoms. These types of interactions strongly depend on the nature of hydrated cations present in alkaline solutions. FIG. 2$b$ summarizes voltammetric and corresponding ICP-MS Pt dissolution profiles of Pt(111) in 0.1 M KOH with and without additional 5 mM of Li$^+$. In line with our previous results, the formation of oxide is significantly shifted towards more positive potentials, with the formation of $OH_{ad}$ enhanced in the presence of Li$^+$ in the same electrolyte. This is reflected in the overall Pt dissolution profile (FIG. 8$b$ and Table 2), which becomes inhibited due to the non-covalent, Li-mediated stabilization of $OH_{ad}$, which in turn results in a lower surface coverage of Pt—$O_{ad}$. As expected, the Pt(111) surface is very stable in the butterfly potential region regardless of the nature of the alkali cation and/or pH of the electrolyte, confirming that the reversible adsorption of $OH_{ad}$ does not trigger Pt dissolution. In contrast, after the formation of Pt—$O_{ad}$ on the surface, the presence of OH$^-$ in alkaline electrolytes also increases the amount of Pt corrosion simply due to bulk complexation effects (Table 2), which is in line with previous reports. Therefore, although alkaline solutions exhibit overall higher Pt dissolution in the early stages of oxide formation as compared with acid solutions, the dissolution rate can be controlled via non-covalent (double layer) effects.

Functional Links Between Activity and Stability

Figures 9A, 9B, 9C:
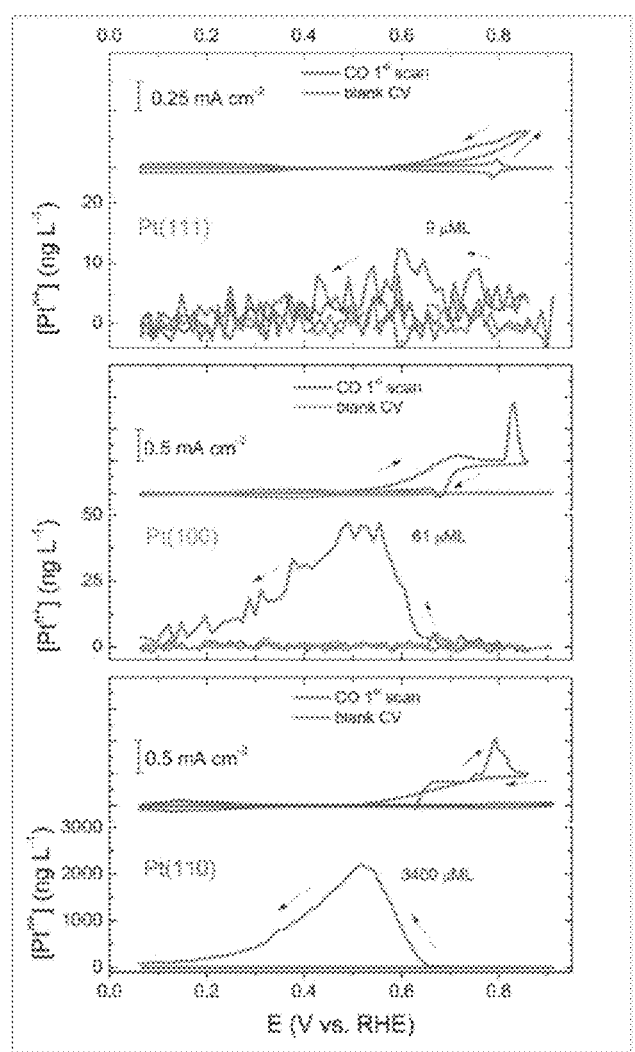
FIGS. 9(A)-9(C) show activity-Stability relationships during Oxygen electrochemistry and CO oxidation electrocatalysis. Effect of distinct reactions on dissolution of Pt surface atoms is shown in FIG. 9(A) during the oxygen reduction reaction (ORR) in FIG. 9(B) the oxygen evolution reaction (OER) and in FIG. 9(C) during the CO oxidation reaction on Pt(111) in 0.1 M $HClO_4$. No dissolution is observed in the presence of $O_2$ or Ar, indicating that Pt surfaces should be stable under continuous ORR catalysis. Unlike for OER, catalysis is takin place with concomitant Pt dissolution and consecutive scans ($1^{st}$ scan, $2^{nd}$ scan) have an effect on activity as well as increased dissolution. This is also relevant in the presence of CO, as subsequent cycles with increasing upper potential limit ($1^{st}$ scan/0.85V, $3^{rd}$ scan/0.90 V, $7^{th}$ scan/1.05 V) already display some Pt dissolution in the cathodic sweep in the potential region where Pt surface is stable under Ar.

Having established the role of covalent and non-covalent interactions in structure-stability relationships, the next consideration was the functional links between the stability of Pt surface atoms and their activity for the ORR (FIG. 9$a$), the OER (FIG. 3$b$), and the CO oxidation reaction (FIG. 9$c$) in acidic solutions. It should be noted that the results summarized in FIGS. 9A-C are obtained during the reaction, thus providing a unique opportunity to follow the kinetics of the reaction and correlate them with surface stability; e.g., to establish in situ stability-reactivity relationships. One particular advantage of using Pt single crystals in the rotating disk configuration is that the kinetic limitations can be separated from mass transport limitations while in the SPRDE one can also simultaneously measure dissolution of surface atoms, as in the case of the ORR and CO oxidation. The second advantage of a rotating configuration is that the kinetics of the OER are not affected by bubble formation, which in the case of a stagnant electrode can disturb the kinetics of the reaction and obstruct the flow path of ions to the ICP-MS in a flow cell configuration.

Figure 17A:
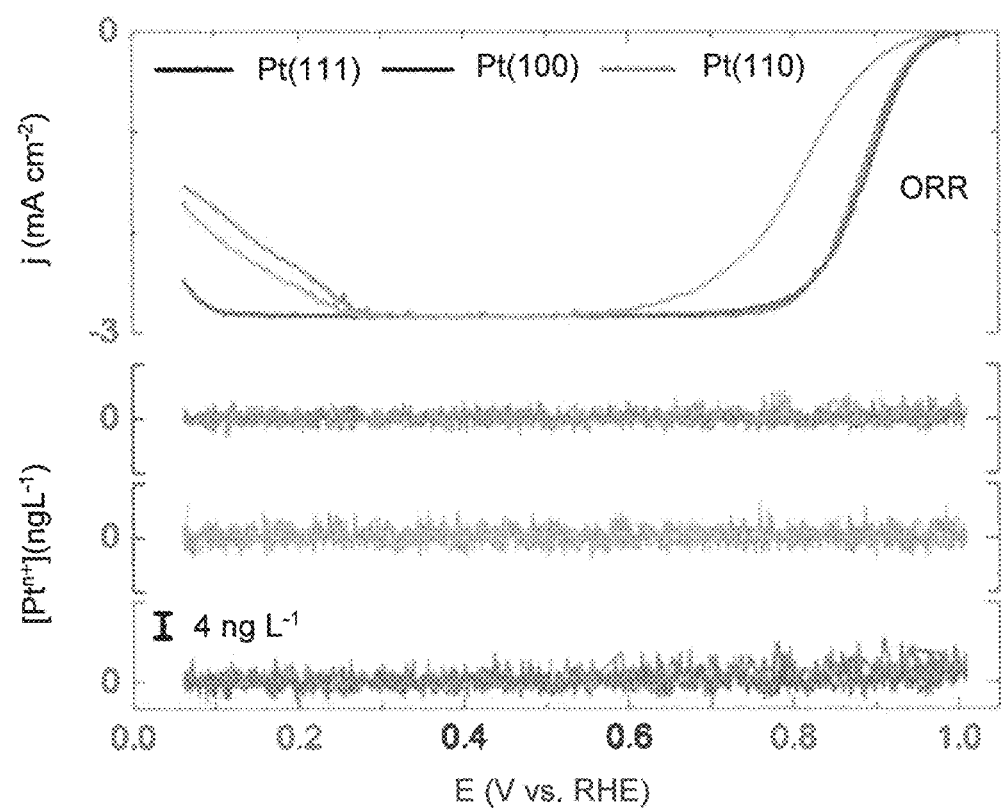
FIGS. 17A-C illustrate Oxygen Reduction Reaction (ORR) and Open Circuit Potential (OCP) measurements accompanied by Pt dissolution monitored by SPRDE-ICPMS on Pt(hkl). At slow sweep rate, c.a. 10 $mVs_{-1}$, dissolution of Pt from Pt(110) is barely observed up to OCP values (FIG. 17A), while none is observed for Pt(111) or Pt(100). OCP experiments shown in FIG. 17B and FIG. 17C depict potential time evolution as soon as the circuit is open (solid lines) with concomitant Pt dissolution observed after oxide formation starts (dashed lines). Note that when $O_2$ is present instantaneous formation of oxide takes place to counter balances the ORR as soon as the circuit is disconnected, with consequent immediate dissolution as shown in dashed lines. But in the presence of Ar, the slow increase in the electrode potential is related to double-layer charging that can still provide enough current to counter balance any residual oxygen still present in the electrolyte, but that is not perceptible from voltammetry itself.
Figure 17B:
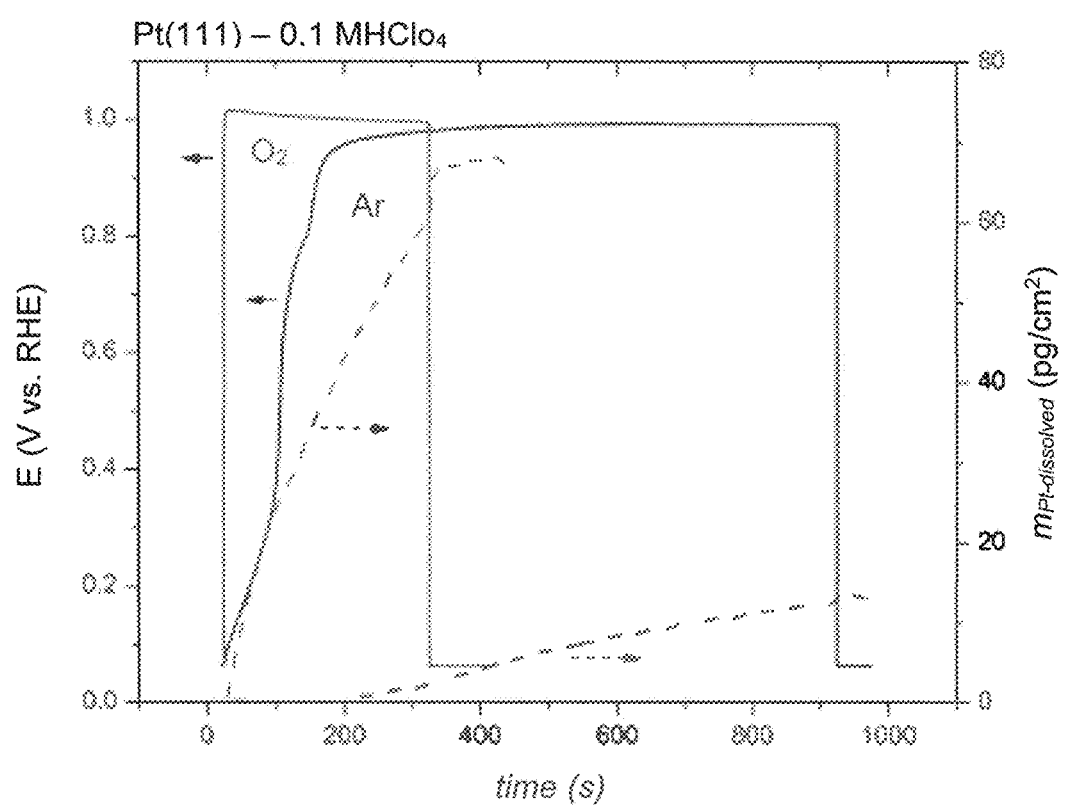
Figure 17C:
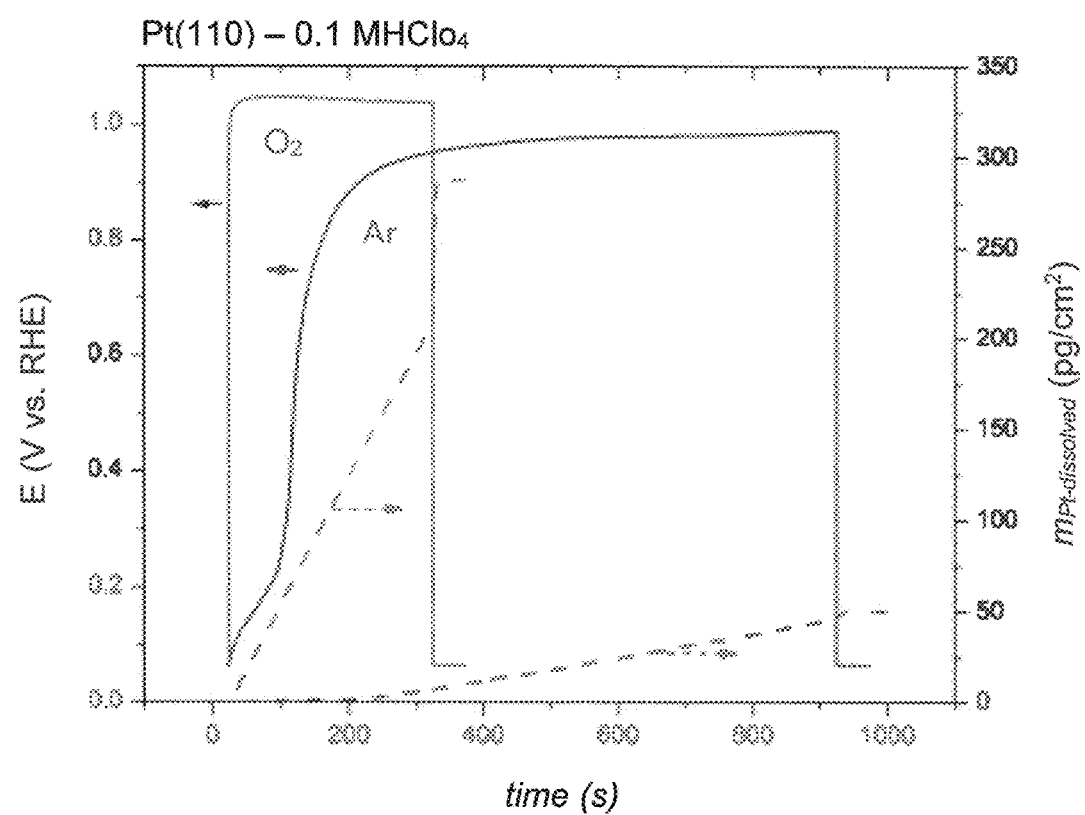
Figure 18:
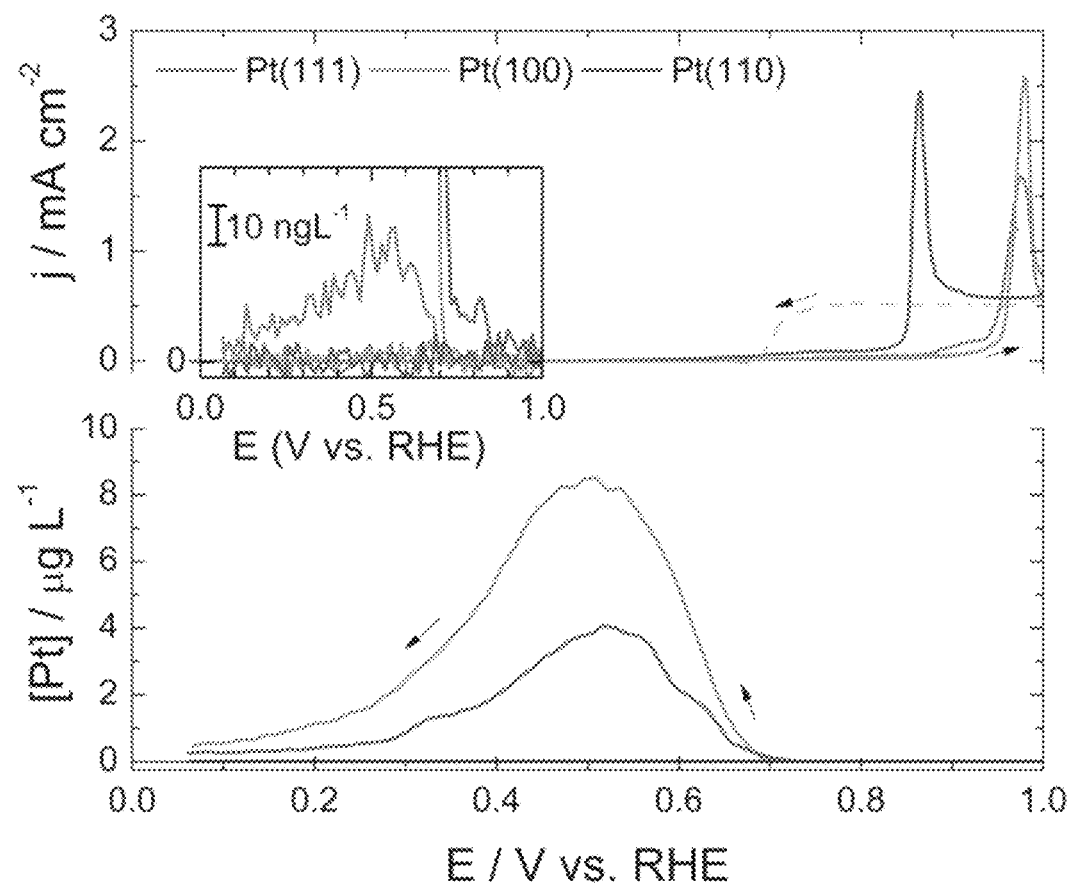
FIG. 18 illustrates CO bulk oxidation measurements on Pt(hkl) surfaces after initial CO-annealing procedure, while monitoring Pt dissolution using SPRDE-ICP-MS. Bulk CO oxidation induces Pt dissolution on the reverse scan as a consequence of the reduction of formed Pt oxide and most likely some Pt carbonyl formation as well. Although Pt dissolution is observed for all three surfaces studied here, Pt(100) shows the highest amount of Pt loss immediately followed by Pt(110) and in much less extent Pt(111) (shown in inset). Similar reverse CO oxidation profile on the reverse is observed on all surfaces (gray dashed line). Scan rate 50 $mVs_{-1}$.

In the case of the ORR, polarization curves recorded on Pt(111) show characteristic current-voltage behavior that is entirely controlled by the adsorption of spectator $OH_{ad}$ and $H_{ad}$ species; e.g., the ORR does not induce irreversible oxide formation. Unsurprisingly, SPRDE-ICPMS unambiguously shows that Pt surface atoms are stable during catalysis and at potentials up to open circuit even in the presence of $O_2$ (FIG. 9$a$). The importance of open circuit conditions should be noted, as the ORR/OER does not form a true reversible redox couple, e.g. the open circuit potential (OCP) for the ORR is determined by $O_2$ reduction and Pt oxide formation instead. As a result, Pt dissolution during the ORR is intrinsically tied to irreversible oxide formation, which implies that Pt is slowly and continuously corroded only at OCP and higher potentials (FIG. 17A-C). However, from results shown in FIG. 17 it can be seen that dissolution of Pt is already taking place at OCP. Note that under an argon atmosphere, the slow increase in the electrode potential until a plateau of small oxide formation is observed is related to positive double-layer charging that provides enough positive current to counter balance the residual oxygen present even in solutions extensively purged by Argon (02 presence not noticeable by voltammetry itself). Not surprisingly, the OCP value for ORR on Pt(111) and Pt(110) is just around 1.0 V, close to the formation of Pt—$O_{ad}$. Nevertheless, these results demonstrate that the ORR does not induce any Pt dissolution while current is being drawn from a fuel cell.

On the opposite side of the activity-stability spectrum is the functional link between the activity of the OER and the stability of Pt(111) surface atoms. Inspection of the upper part of FIG. 3$b$ indicates that the OER always takes place in the same potential region where the surface is covered with an irreversible oxide. On the other hand, the bottom part of FIG. 9$b$ shows that Pt dissolution begins at potentials above 1.2 V in the anodic scan, and takes place continuously during the OER above 1.5 V. Importantly, in a non-adsorbing electrolyte such as perchloric acid it is not believe that there will be any complexation effects that would trigger anodic dissolution at higher electrode potentials (as observed on the presence of CI in FIG. 8$a$).

Therefore, anodic dissolution could be linked to the formation of Pt in higher oxidation states (e.g. 4+), in a similar fashion as has been observed for Ir and Ru surfaces. Although the morphology of the oxide structure being formed (occurrence of "place exchange") could also account for this dissolution behavior, it is not expected it to be a major process as any appreciable atomic movement would be somewhat limited at sweep rates of 50 mVs$^{-1}$. Nonetheless, the fact that the equivalent current density of Pt ion formation in the anodic scan is orders of magnitude smaller than the respective OER current density observed from CVs indicates that the OER is indeed always accompanied by the simultaneous dissolution of surface atoms, and that $O_2$ evolution might take place, with high turnover rates, at surface sites that are opened after Pt dissolution. In support of this, it was observed that upon reversing the scan direction, the dissolution rates of Pt is extremely high during the reduction of irreversible oxide (inset of FIG. 8$b$); introducing defects that significantly enhance the OER in the second sweep, but at the expense of higher dissolution rates of surface atoms. Therefore, this confirms that the activity of surface atoms is inversely proportional to their stability, and suggest that it is very difficult (impossible) to unambiguously establish relationships between the electronic properties of the substrate and measured activities without taking into account dissolution of the substrate surface atoms. This observation strongly indicates that the best materials for the OER must strike a balance between activity and stability.

Having established close ties between the stability of Pt(hkl) surfaces and the formation of Pt—$OH_{ad}$ and Pt—$O_{ad}$, and having further explored these effects for the ORR and OER, the next consideration is the activity-stability relationships for the bulk CO oxidation reaction, which is assumed to consume $OH_{ad}$ through the Langmuir-Hinshelwood mechanism. The most active sites for the reaction are Pt ad-islands, which are inherently present on every Pt single crystal.

CO oxidation on Pt(111) exhibits an unusual sweep-dependent deactivation; namely, the highest activity is observed during the very first sweep with the reactivity in the so-called pre-ignition region (between 0.6 V and 0.85 V) attenuated after every consecutive sweep until no activity is observed on the fifth sweep. Although this deactivation behavior is still puzzling, STM images recorded before and after CO oxidation suggest that $CO_{ad}$ may enhance the mobility of the most active Pt ad-islands so that the beneficial, low coordination Pt atoms slowly diffuse on the surface until they incorporate at step-edge sites. Considering that recent findings show that CO affects Pt dissolution when Pt—$O_{ad}$ is present, C O bulk oxidation and Pt corrosion on Pt(111) were simultaneously monitored, as depicted in FIG. 9c. Surprisingly, during the first cycle in a CO saturated solution, Pt ions are already observed by ICP-MS even though the upper potential limit (ca. 0.85 V) is still well below the region where the formation of an irreversible oxide takes place on bare Pt(111) (FIGS. 7A and 9c). As expected, increasing the positive potential limit to 0.9 and then 1.05 V, where the sharp CO oxidation peak is observed, is mirrored by increasingly higher dissolution rates during the negative-going sweep and steady deactivation of the pre-ignition region. Notice also that the amount of dissolved Pt in the presence of CO substantially exceeds the level of Pt dissolution observed in Ar saturated solutions (see FIG. 7A and FIG. 9c).

Thus, it is believed this provides an indication of the role of CO on stability of Pt surface atoms. First, dissolution is initiated after going up to the reversible-irreversible potential region (0.85-1.0V), signaling that some Pt may be in the ionic form required for Pt dissolution (irreversible oxide with formation of $Pt^{2+/4+}$). Second, CO interacts very strongly with Pt, leading to a high degree of relaxation of Pt surface atoms (ca. 4%), and most likely, weakening of the Pt—Pt bond. Although still hypothetical, it is believed that the combination of structural/energetic (CO-induced relaxation) and chemical (oxidation state of Pt) factors may indeed control the dissolution of Pt in this potential region.

Regardless, based on the results shown in FIG. 9c it is reasonable to propose that the so-called CO-annealing of metal surfaces is a process that is governed by CO oxidation-induced preferential dissolution of the low coordinated defect sites, rather than enhanced Pt atoms mobility that aggregates at step-edges.

Temperature Gradient Study

Figure 10:
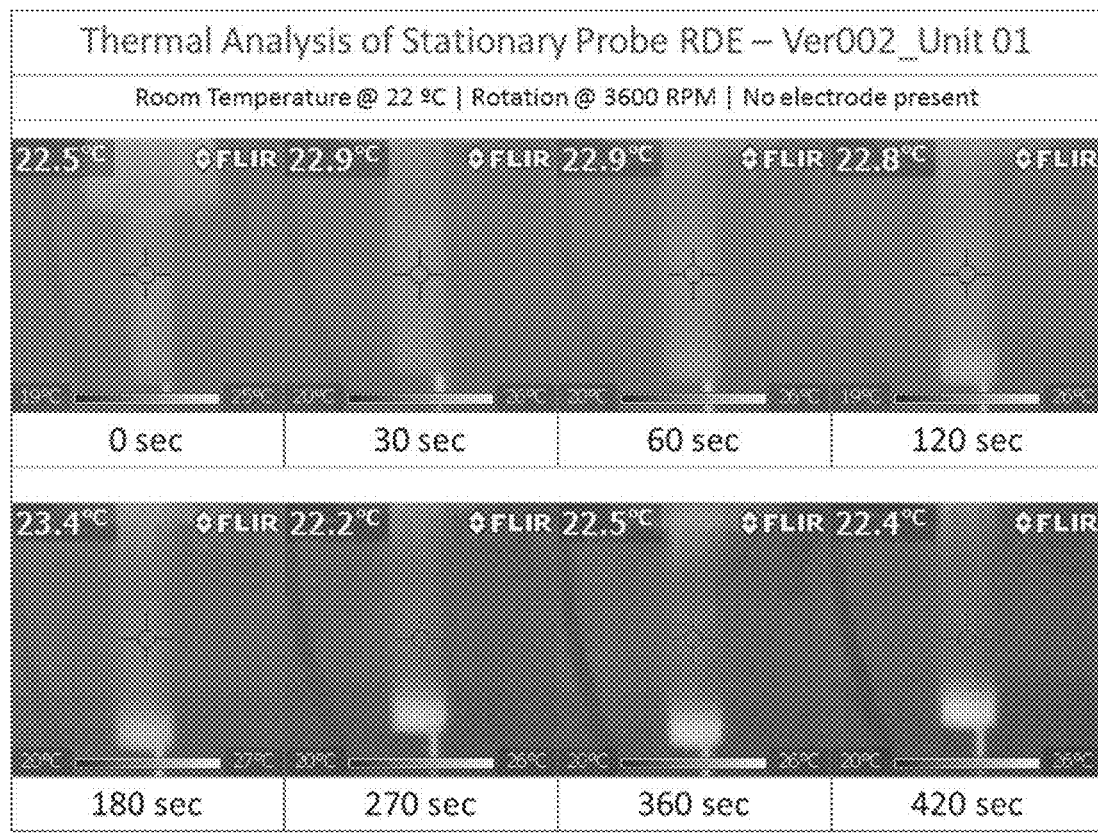
FIG. 10 shows the results of a thermal analysis study using a thermal camera enabled investigation of temperature gradients generated once the probe is in use.

The use of a thermal camera (FIG. 10) enabled investigation of temperature gradients generated once the probe is in use. As one can see from the pictures above, only the tip of the probe system develops a small gradient temperature over time at rotation speeds greater than already recommended by the rotator manufacturer. Such extreme conditions of electrode rotation were employed to demonstrate the thermal stability of the probe system, since only a slight increase of about 4 to 5° C. was observed at the test conditions. Nonetheless, this results was used to feedback the probe design to reduce even further any thermal gradient generated while usage of the SPRDE system. The new system is shown in the technical drawings attached.

Rotation Rate Study

Figure 11:
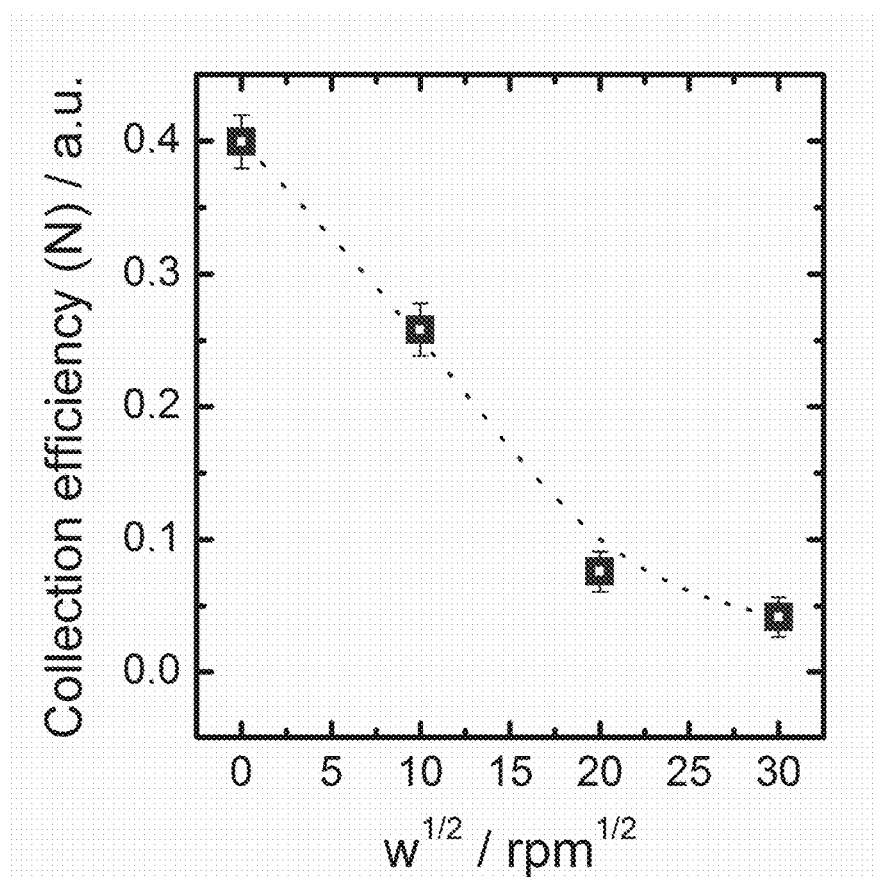
FIG. 11 shows sensitivity or collection Efficiency dependence on rotation rate.

FIG. 11 shows sensitivity or collection Efficiency dependence on rotation rate. Due the very nature of the probe system with respect to the hydrodynamic conditions of the rotating electrode, the balance between dragging flow towards the electrode and the flow through the probe that collects the species and transport it to the analytical instrument inlet results in a dependence of the fraction of species collected on the probe according to the electrode rotation rate. This dependence of the collection efficiency or the sensitivity of the probe, to the rotation rate is shown above. It is clear the effect of reduced sensitivity at higher rotation rates, ca. 900 rpm. Nonetheless, the fact that sensitivity levels around 25% at 100 rpm can be achieved demonstrates the successful nature of the probe system.

Figures 12A, 12B:
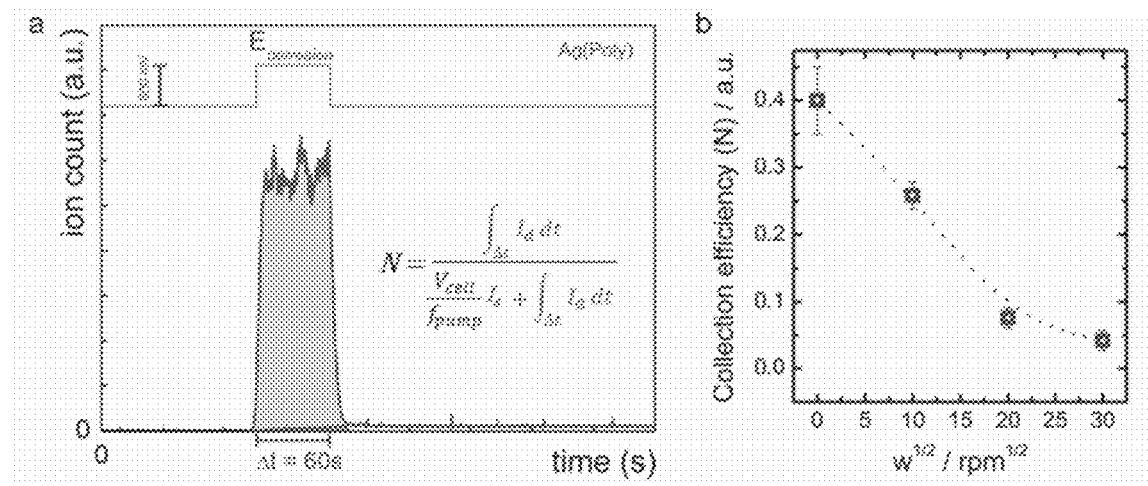
FIGS. 12A-B show experimental determination of the SPRDE collection efficiency (N).
Figure 13A:
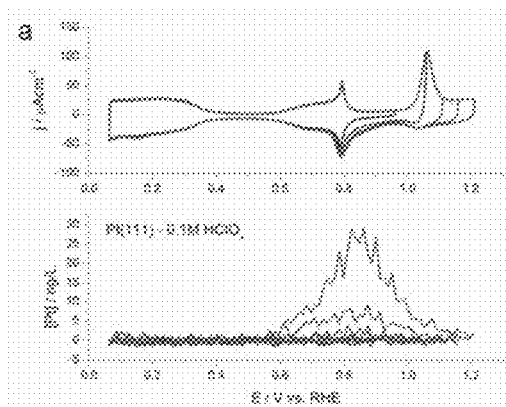
FIGS. 13A-D show cyclic voltammetry and corresponding dissolution profile of several distinct Pt surface morphologies.
Figure 13B:
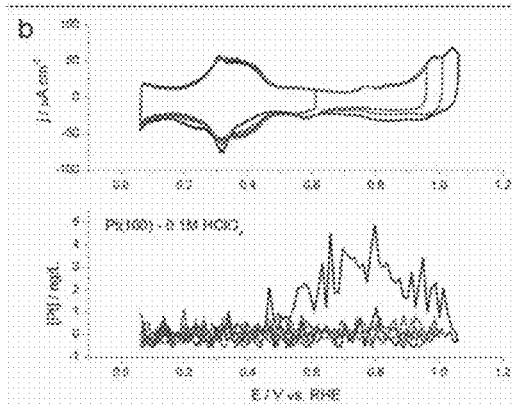
Figure 13C:
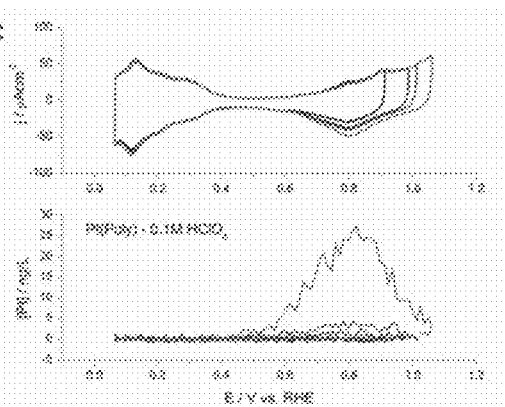
Figure 13D:
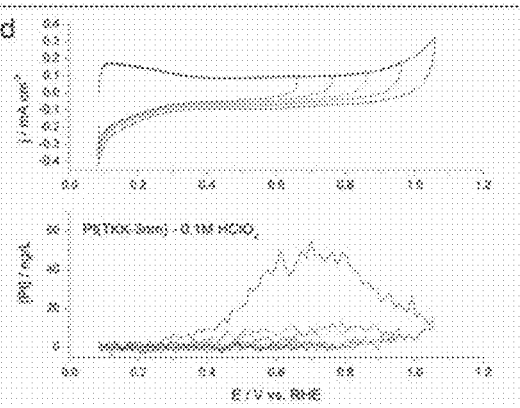

As it only collects a fraction of the ions produced at the surface, it is necessary to determine the collection efficiency (N) for the system (FIG. 12A-B). For that a Ag polycrystalline electrode was, as its continuous dissolution at electrode potentials above 0.6 V vs. RHE can be used to correlate corrosion current (univalent cation, Ag+) and concentration of silver ions in solution measured by external standard solutions (Method A).

Another way of obtaining the value of N is by correlating the dissolution profile under a corrosion potential step, as shown in FIG. 12A, and making use of mass balance to account for the fact that part of the ions generated from the surface will go to the probe and the remaining will go to the bulk of the electrolyte contained in the cell (Method B). To avoid any complications from a decrease in the total cell volume due to continuous electrolyte removal by the SPRDE, the electrolyte is replenished at the same flow rate that it is being removed by using a distinct channel from the peristaltic pump (ESI MP2 micro peristaltic pump). In this way it ensures that the overall cell volume is fixed (ca. 60 mL) and that for a fixed flow rate (ca. 7.5 μL s−1) one can correlate the area under the corrosion pulse (+IdΔtdt) with the offset in the background signal measured after the potential pulse is over (Iσ). This method does not require pre-calibration of the instrument to know absolute concentrations or any correlation with previous knowledge of the passed electric charge corresponding to dissolution, but it does require that the amount of generated ions is large enough to create an offset in the background levels. Note that due to the relatively large cell volume, and considering the ICPMS detection limit of 2 ppt, a minimum concentration corresponding to a fraction of the surface atoms of about 1 thousandth of a monolayer can be detected (using an average of 425 ng cm-2 of Pt surface mass density for 1 monolayer). Therefore, for small amounts of dissolved ions (of the order of pg cm-2), the increase in background signal is negligible. Both methods give equivalent results for N (<0.5% difference).

Unlike the ring-disk method, where N is independent of rotation rate, both electrode rotation speed (w) and probe flow rate (fpump) can change the collection efficiency due the hydrodynamic flow balance between electrode drag (either under constant rotation or due to hydrodynamic continuity without rotation) and probe pumping electrolyte out at a fixed flow rate. This can be seen in FIG. 12b, where changes in collection efficiency are observed for a given rotation rate. Without any electrode rotation, no reliable hydrodynamic conditions can be established, rendering the collection efficiency high but with added noise in the concentration measurements. On the other hand, in the presence of continuous rotation, the collection efficiency decreases continuously for increasing rotation rates, but a steady flow can be achieved. The flow through the pump does not affect the diffusion layer (Nernst layer) at the electrode surface, as it is located further from the typical Nernst thickness, which renders the same hydrodynamic properties for the RDE method unaltered. Therefore the pump flow rate was kept constant at 7.5 μL s−1 in order to minimize any delay time from the electrode all the way to the ICPMS nebulizer system (typically 5.5 seconds), all experiments shown in the manuscript were taken at a rotation speed of 100 rpm, which gives N=0.25±0.02.

Experiment Conclusions

In conclusion, described herein is a newly developed probe that enables the use of our surface science-based approach in order to examine the elusive relationships between surface stability and the atomic-level surface structure of platinum single crystals. By examining such relationships in aqueous environments containing controlled amounts of anions (e.g., Cl⁻) and cations (e.g., Li⁺) in acid and alkaline solutions, respectively, it was possible to independently examine the impact of covalent and non-covalent interactions in guiding the dissolution of Pt. By examining the in situ dissolution rates of platinum single crystal surfaces in Cl⁻-free electrolytes and in the presence of small amounts of it was found that the overall dissolution rate is driven by a synergy between electrochemical (potential-induced oxide formation) and chemical (thermodynamic driving force for Pt complexation with Cl⁻) corrosion. Moreover, for alkaline solutions, it was also found that besides expected pH effect, non-covalent interactions of Li⁺ cations present in the double layer with Pt—$OH_{ad}$ leads to an inhibition of Pt oxide formation, yielding a small, yet clearly discernable, effect on platinum dissolution. Overall, it was observed that in non-specifically adsorbing acid electrolytes, dissolution is triggered by the potential-dependent transformation of the Pt valence state from the reversible formation of $Pt^{\delta+}$—$OH_{ad}^{\delta-}$ to the $_{m-}$ irreversible formation of $Pt_x^{n+}O_y^{m-}$. Careful examination of this transformation made it possible to develop structure-stability relationships for platinum single crystals, an insight that can be used as a foundation for understanding the stability of polycrystalline Pt and Pt nanoparticles. This insight further served as foundation to understand how the dissolution dynamics are strongly affected by the nature of the electrochemical reaction performed; e.g., continuous dissolution of Pt ions during the oxygen evolution reaction (OER), limited dissolution of low coordinated Pt ad-islands during the CO oxidation reaction, and no dissolution during the oxygen reduction reaction (ORR).

Definitions

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A stationary probe rotating disk electrode comprising:
   a stationary probe, with a passage therethrough, having a probe holder and a probe engageable with the probe holder, the probe having a probe body with a probe opening and a probe tip;
   a rotating disk electrode comprising a rotating shaft, rotatable about a longitudinal axis, and an electrode having a distal end with an electrode disposed therein, the rotating disk electrode rotatably positioned within the passage of the stationary probe with the electrode disposed within the probe; and
   the probe tip extends from the probe body apart from the electrode, the probe tip extending inward a first distance from a circumference of the probe body and extending above the electrode a second distance, the first distance being less than a diameter of the probe body, the probe tip having a capillary entrance spaced apart from the electrode a first distance, the capillary entrance connected to an analyte flow path.

2. The stationary probe rotating disk electrode of claim 1, wherein the probe is removably engageable with the probe holder.

3. The stationary probe rotating disk electrode of claim 2 wherein the probe holder includes a plurality of alignment rods engagable with a plurality of openings in the probe.

4. The stationary probe rotating disk electrode of claim 3, wherein the probe holder includes a plurality of probe holder magnets engageable with a plurality of probe magnets of the probe.

5. The stationary probe rotating disk electrode of claim 1, further comprising a plurality of probe tips each spaced apart and extending from the probe body.

6. The stationary probe rotating disk electrode of claim 1, further in communication with an analytical instrument having tubing in communication with the analyte fluid path.

7. The stationary probe rotating disk electrode of claim 1, wherein the probe holder further includes a probe holder nut.

8. The stationary probe rotating disk electrode of claim 1, wherein the capillary entrance is positioned with an analyte flow path therethrough that is perpendicular to a surface normal of the electrode.

9. The stationary probe rotating disk electrode of claim 1, wherein the rotating disk electrode comprises an electrode portion and the electrode is disposed therein, the electrode portion rotatably positioned within the probe.

10. An analytical system comprising:
an analytical instrument having an analyte flow intake;
a stationary probe rotating disk electrode comprising:
a stationary probe having a probe holder and a probe with a probe body and a probe tip;
a rotating disk electrode comprising a rotating shaft, rotatable about a longitudinal axis, and having an electrode portion extending therefrom configured to receive an electrode;
the probe tip extending from the probe body apart from the rotating shaft at an electrode end and having a capillary entrance spaced apart from the electrode end a first distance, the capillary entrance connected to an analyte flow path;
the probe holder configured to engage with the probe, the probe holder and probe having passage there through configured to receive the rotating shaft, the probe hold secured relative to the rotating disk electrode to define a distance between the electrode and the probe tip with the rotating shaft rotatable within the probe holder;
wherein the analyte flow path is in fluid communication with the analyte flow intake.

11. The analytical system of claim 10 wherein the probe holder includes a plurality of alignment rods engagable with a plurality of openings in the probe.

12. The analytical system of claim 11, wherein the probe holder includes a plurality of probe holder magnets engageable with a plurality of probe magnets of the probe.

13. The analytical system of claim 10, further comprising a plurality of probe tips each spaced apart and extending from the probe body.

14. The analytical system of claim 10, wherein the probe holder further includes a probe holder nut.

15. The analytical system of claim 10, wherein the analyte flow path is perpendicular to a surface normal of the electrode.

16. The analytical system of claim 10, wherein the rotating disk electrode comprises an electrode portion and the electrode is disposed therein, the electrode portion rotatably positioned within the probe.

17. The analytical system of claim 16, wherein the electrode portion is removably engagable with the rotating shaft.

18. A stationary probe rotating disk electrode comprising:
a stationary probe, with a passage therethrough, having a probe holder and a probe engageable with the probe holder, the probe having a probe body with a probe opening and a probe tip;
a rotating disk electrode comprising a rotating shaft, rotatable about a longitudinal axis, and an electrode having a distal end with an electrode disposed therein, the rotating disk electrode rotatably positioned within the passage of the stationary probe with the electrode disposed within the probe; and
the probe tip extends from the probe body apart from the electrode and having a capillary entrance spaced apart from the electrode a first distance, the capillary entrance connected to an analyte flow path,
wherein the probe is removably engageable with the probe holder, and
wherein the probe holder includes a plurality of alignment rods engagable with a plurality of openings in the probe.

19. A stationary probe rotating disk electrode comprising:
a stationary probe, with a passage therethrough, having a probe holder and a probe engageable with the probe holder, the probe having a probe body with a probe opening and a plurality of probe tips each spaced part and extending from the probe body;
a rotating disk electrode comprising a rotating shaft, rotatable about a longitudinal axis, and an electrode having a distal end with an electrode disposed therein, the rotating disk electrode rotatably positioned within the passage of the stationary probe with the electrode disposed within the probe; and
each of the plurality of probe tips extends from the probe body apart from the electrode and have a capillary entrance spaced apart from the electrode a first distance, the capillary entrance connected to an analyte flow path.

20. A stationary probe rotating disk electrode comprising:
a stationary probe, with a passage therethrough, having a probe holder and a probe engageable with the probe holder, the probe having a probe body with a probe opening and a probe tip;
a rotating disk electrode comprising a rotating shaft, rotatable about a longitudinal axis, and an electrode having a distal end with an electrode disposed therein, the rotating disk electrode rotatably positioned within the passage of the stationary probe with the electrode disposed within the probe; and
the probe tip extends from the probe body apart from the electrode and having a capillary entrance spaced apart from the electrode a first distance, the capillary entrance connected to an analyte flow path,
wherein the stationary probe rotating disk electrode is in communication with an analytical instrument having tubing in communication with the analyte fluid path.

* * * * *